US011521706B2

(12) United States Patent
Xin et al.

(10) Patent No.: US 11,521,706 B2
(45) Date of Patent: Dec. 6, 2022

(54) TESTING AND REPRESENTING SUSPICION OF SEPSIS

(71) Applicant: Beckman Coulter, Inc., Brea, CA (US)

(72) Inventors: Rongchang Xin, Palmetto Bay, FL (US); Carlos A. Ramirez, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 426 days.

(21) Appl. No.: 16/390,648

(22) Filed: Apr. 22, 2019

(65) Prior Publication Data

US 2019/0324036 A1   Oct. 24, 2019

Related U.S. Application Data

(63) Continuation-in-part of application No. 15/987,541, filed on May 23, 2018.

(60) Provisional application No. 62/660,795, filed on Apr. 20, 2018.

(51) Int. Cl.
| | |
|---|---|
| *G16B 5/20* | (2019.01) |
| *G16B 40/00* | (2019.01) |
| *G16B 50/20* | (2019.01) |
| *G01N 33/569* | (2006.01) |
| *G01N 33/68* | (2006.01) |
| *G01N 33/50* | (2006.01) |
| *G16B 45/00* | (2019.01) |
| *G16H 10/40* | (2018.01) |
| *G01N 15/00* | (2006.01) |
| *G01N 33/48* | (2006.01) |
| *A61B 5/00* | (2006.01) |

(52) U.S. Cl.
CPC .............. *G16B 5/20* (2019.02); *G16B 40/00* (2019.02); *G16B 50/20* (2019.02); *A61B 5/00* (2013.01); *G01N 33/48* (2013.01); *G01N 33/50* (2013.01); *G01N 33/5094* (2013.01); *G01N 33/56911* (2013.01); *G01N 33/56972* (2013.01); *G01N 33/6893* (2013.01); *G01N 2015/008* (2013.01); *G01N 2800/26* (2013.01); *G16B 45/00* (2019.02); *G16H 10/40* (2018.01)

(58) Field of Classification Search
None
See application file for complete search history.

(56) References Cited

U.S. PATENT DOCUMENTS

| | | | |
|---|---|---|---|
| 5,125,737 A | 7/1992 | Rodriquez et al. | |
| 5,341,291 A | 8/1994 | Roizen, III et al. | |
| 5,529,933 A | 6/1996 | Young et al. | |
| 6,228,652 B1 | 5/2001 | Rodriquez et al. | |
| 6,509,192 B1 | 1/2003 | Young | |
| 7,109,036 B2 | 9/2006 | Ortiz et al. | |
| 7,135,341 B2 | 11/2006 | Ortiz et al. | |
| 7,176,031 B2 | 2/2007 | Li et al. | |
| 7,195,919 B2 | 3/2007 | Jacobs et al. | |
| 7,285,417 B2 | 10/2007 | Ortiz et al. | |
| 7,390,662 B2 | 6/2008 | Riley et al. | |
| 7,393,688 B2 | 7/2008 | Ortiz et al. | |
| 8,094,299 B2 | 1/2012 | Wells et al. | |
| 8,189,187 B2 | 5/2012 | Graham et al. | |
| 8,221,995 B2 | 7/2012 | Lee et al. | |
| 8,719,053 B2 | 5/2014 | Showalter et al. | |
| 9,939,453 B2 | 4/2018 | Lu et al. | |
| 10,221,453 B2 | 3/2019 | Shi et al. | |
| 2001/0051879 A1 | 12/2001 | Johnson et al. | |
| 2001/0051880 A1 | 12/2001 | Schurenberg et al. | |
| 2003/0105648 A1 | 6/2003 | Schurenberg et al. | |
| 2004/0042471 A1 | 3/2004 | Yung et al. | |
| 2004/0220761 A1 | 11/2004 | Yundt-Pacheco | |
| 2004/0267562 A1 | 12/2004 | Fuhrer et al. | |
| 2005/0022103 A1 | 1/2005 | Yundt-Pacheco | |
| 2005/0159982 A1 | 7/2005 | Showalter et al. | |
| 2008/0186134 A1 | 8/2008 | Parkhurst et al. | |
| 2009/0149724 A1 | 6/2009 | Mark et al. | |
| 2011/0046910 A1 | 2/2011 | Haas et al. | |
| 2011/0076685 A1 | 3/2011 | Moeller et al. | |
| 2011/0166794 A1 | 7/2011 | Linssen et al. | |

(Continued)

FOREIGN PATENT DOCUMENTS

| | | |
|---|---|---|
| CN | 102033035 B | 11/2013 |
| EP | 1021701 | 7/2000 |

(Continued)

OTHER PUBLICATIONS

Petrak, RM, et al. "The value of an infectious diseases specialist." Clinical infectious diseases 36.8 (2003): 1013-1017.*
Nachimuthu, Senthil K., and Peter J. Haug. "Early detection of sepsis in the emergency department using Dynamic Bayesian Networks." AMIA Annual Symposium Proceedings. Vol. 2012. American Medical Informatics Association, 2012.*
Chaves, Fernando, Bethany Tierno, and Dongsheng Xu. "Neutrophil vol. distribution width: a new automated hematologic parameter for acute infection." Archives of pathology & laboratory medicine 130.3 (2006): 378-380.*

(Continued)

*Primary Examiner* — G Steven Vanni
(74) *Attorney, Agent, or Firm* — Frost Brown Todd LLC

(57) ABSTRACT

Embodiments of the present technology include a method for testing a blood sample for sepsis. The method may include receiving a blood sample from an individual. The method may also include executing an instruction to analyze the blood sample for sepsis. In addition, the method may include measuring values of a set of characteristics in the blood sample. The set of characteristics being determined prior to measuring the values. The method may further include analyzing the values of the set of characteristics to produce a representation of a suspicion of sepsis. In addition, the method may include displaying the representation. Embodiments also include systems for testing blood sample for sepsis.

15 Claims, 6 Drawing Sheets

(56) References Cited

U.S. PATENT DOCUMENTS

| | | |
|---|---|---|
| 2012/0109531 A1 | 5/2012 | Knafel et al. |
| 2012/0109682 A1 | 5/2012 | Seltzer et al. |
| 2013/0197943 A1 | 8/2013 | Conlin et al. |
| 2013/0246079 A1 | 9/2013 | Hoffman et al. |
| 2014/0084930 A1 | 3/2014 | Dodds |
| 2014/0160464 A1 | 6/2014 | Han |
| 2014/0172321 A1 | 6/2014 | Han |
| 2015/0338427 A1 | 11/2015 | Pollack et al. |
| 2016/0168638 A1 | 6/2016 | Garrett et al. |
| 2016/0356801 A1 | 12/2016 | Glavina et al. |
| 2017/0285624 A1 | 10/2017 | Lesher |
| 2019/0128906 A1 | 5/2019 | Ramirez et al. |
| 2019/0324035 A1 | 10/2019 | Magari et al. |
| 2019/0362824 A1 | 11/2019 | Xin et al. |
| 2019/0383800 A1 | 12/2019 | Careaga et al. |
| 2021/0007675 A1 | 1/2021 | Tejidor et al. |
| 2021/0010924 A1 | 1/2021 | Tejidor et al. |
| 2021/0011005 A1 | 1/2021 | Tejidor et al. |

FOREIGN PATENT DOCUMENTS

| | | |
|---|---|---|
| EP | 1718966 | 11/2006 |
| JP | 2012-529033 A | 11/2012 |
| KR | 20150036329 A | 4/2015 |
| KR | 20150091049 A | 8/2015 |
| WO | WO 88/07198 A1 | 9/1988 |
| WO | WO 2004/044556 A2 | 5/2004 |
| WO | WO 2012/139047 A2 | 10/2012 |
| WO | WO 2014/028534 A2 | 2/2014 |
| WO | 2014/084930 | 6/2014 |
| WO | WO 2014/154810 A1 | 10/2014 |
| WO | WO 2017/132132 | 8/2017 |
| WO | WO 2019/028448 A1 | 2/2019 |

OTHER PUBLICATIONS

Coulter, "Coulter® 3-D VCS Technology," downloaded Feb. 11, 2022 from (http://www.cyto.purdue.edu/cdroms/cyto2/6/coulter/ss000125.htm), Beckman Coulter, Inc., Fullerton, CA, 3 pages, 1996.*

"Biomarker," The Pharmaceutical Society of Japan, a pharmaceutical science glossaty, 2008, 2 pgs.

"Red Blood Cell Distribution With (RDW): Definition and Calculation—LabCE.com, Laboratory Continuing Education," Nov. 2012, downloaded Aug. 22, 2019 from: https://labce.com/spg579122_red_blood_cell_distribution_width_rdw_definition_a.aspx , 1pg.

Sukhacheva, et al., "The Role of Monocytes in the Progression of Sepsis," Beckman Coulter, 2018, downloaded Aug. 22, 2019 from: media.beckmancoulter.com/-/media/diagnostics/products/hematology/early-sepsis-indicator/docs/role-of-monocytes-for-progression-of-sepsis-en.pdf, 12 pgs.

Zhou, et al., "VCS parameters of neutrophils, monocytes and lymphocytes may indicate local bacterial infection in cancer patients who accepted cytotoxic chemotherapeutics," Eur J Clin Microbiol Infect Dis, 2016, 35:41-48, 8 pgs.

Zonneveld, R., et al., "Analyzing Neutrophil Morphology, Mechanics, and Motility in Sepsis: Options and Challenges for Novel Bedside Technologies," Crit Care Med, 2016, 44(1):218-228, 11 pgs.

European Examination Report dated Oct. 15, 2020 for Application No. EP 17704357.7, 10 pgs.

International Search Report and Written Opinion dated Aug. 23, 2019 for International Application No. PCT/US2019/028488, 10 pgs.

International Search Report and Written Opinion dated Oct. 20, 2020 for International Application No. PCT/US2020/041535, 12 pgs.

International Search Report and Written Opinion dated Oct. 8, 2020 for International Application No. PCT/US2020/041548, 10 pgs.

International Search Report and Written Opinion dated Oct. 5, 2020 for International Application No. PCT/US2020/041541, 10 pgs.

Japanese Office Action, Notice of Reasons for Refusal, dated Oct. 29, 2020 JP 2018-538892, 27 pgs.

U.S. Office Action, Restriction Requirement, dated Apr. 7, 2021 for U.S. Appl. No. 15/987,541, 5 pgs.

U.S. Office Action, Non-Final Rejection, dated Jul. 31, 2020 for U.S. Appl. No. 16/073,757, 23 pgs.

U.S. Office Action, Notice of Allowance, dated Feb. 8, 2021 for U.S. Appl. No. 16/073,757, 20 pgs.

International Search Report and Written Opinion dated Apr. 20, 2017 for International Application No. PCT/US2017/014708, 16 pages.

International Search Report and Written Opinion dated May 4, 2018 for International Application No. PCT/US2018/020087, 13 pages.

International Search Report and Written Opinion dated Mar. 26, 2019 for International Application No. PCT/US2018/057645, 16 pages.

International Search Report and Written Opinion dated Aug. 2, 2019 for International Application No. PCT/US2019/028487, 7 pages.

International Search Report and Written Opinion dated Aug. 20, 2019 for International Application No. PCT/US2019/031151, 9 pages.

International Search Report and Written Opinion dated Sep. 4, 2019 for International Application No. PCT/US2019/028486, 11 pages.

U.S. Non-Provisional U.S. Appl. No. 16/488,503, entitled "Cross Discipline Disease Management System," filed Aug. 23, 2019.

Aird; William C., "The Hematologic System as a Marker of Organ Dysfunction in Sepsis", Mayo Clin Proc., Jul. 2003;78:869-881, 2003 *Mayo Foundation for Medical Education and Research*.

Anonymous, "Multiple Logistic Regression Analysis", Jan. 17, 2013, retrieved from http://sphweb.bumc.cu.edu/otlt/MPH-Modules/8S/8S704_Multivariable/8S704_Multivariables8.html.

Bhargava, et al. "Elevated mean neutrophil volume+ CRP is a highly sensitive and specific predictor of neonatal sepsis", Letter to the Editor, International Journal of Laboratory Hematology, DOI: 10.1111/iijh.12120, 2013, 4 pages.

Celik, et al., "Automated determination of neutrophil VCS parameters in diagnosis and treatment efficacy of neonatal sepsis", Pediatric Research, vol. 71, No. 1, Jan. 2012, pp. 121-125.

Chaves, et al. "Neutrophil Volume Distribution Width: A New Automated Hematologic Parameter for Acute Infection", Arch Pathol Lab Med, vol. 130. Mar. 2006, pp. 378-380.

Chaves, et al. Quantitative Determination of Neutrophil VCS Parameters by the Coulter Automated Hematology Analyzer: New and Reliable Indicators for Acute Bacterial Infection. American Journal Clinical Pathology, 2005, 124:440-444, DOI, 10.1309/LLF75WOFWQQ8TCC5.

Cho, et al., "Biomarkers of Sepsis", Infection & Chemotherapy, Feb. 2014; 46:1-12.

Crouser, et al., "Improved Early Detection of Sepsis in the ED with a Novel Monocyte Distribution Width Biomarker", 152#3 CHEST, Sep. 2017, pp. 518-526.

Dellinger, et. al. "Surviving Sepsis Campaign: International Guidelines for Management of Severe Sepsis and Septic Shock, 2012", Intensive Care Medicine, 2013, 39:164-228, DOI 10.1007/s00134-012-2769-8.

Dilmoula, et al., "Volume Conductivity and Scatter Properties of Leukocytes (VCS Technology) in Detecting Sepsis in Critically III Adult Patients", Blood (ASH annual Meeting Abstracts) 2011; 118: Abstract 4729, 3 pages.

Early Sepsis Indicator Application Addendum UniCel DxH 900 Coulter Cellular Analysis System, Beckman Coulter, published Version: v1, Available online at: https://www.analis.be/site/objects/media/0/0/8/1/9/0081990_media/media1 .pdf, Apr. 26, 2018, 38 pages.

Ferrer, et al., "Emperic Antibiotic Treatment Reduces Mortality in Severe Sepsis and Septic Shock From the First Hour: Results From a Guideline-Based Performance Improvement Program", Critical Care Medicine, Aug. 2014, vol. 42, No. 8, pp. 1749-1755.

Gaieski, et al., "Impact of time to antibiotics on survival in patients with severe sepsis or septic shock in whom early goal-directed

(56) References Cited

OTHER PUBLICATIONS therapy was initiated in the emergency department", Critical Care Medicine, 2010, vol. 38, No. 4, pp. 1045-1053.

Garnacho-Montero, et al., "Impact of adequate empirical antibiotic therapy on the outcome of patients admitted to the intensive care unit with sepsis", Critical Care Medicine, 2003;31 :2742-51.

Gea-Banecloche, et al. "Sepsis associated with immunosuppressive medications: An evidence-based review" Critical Care Medicine 2004;32:S578-S590.

Glickman, et al., Disease Progression in Hemodynamically Stable Patients Presenting to the Emergency Department With Sepsis. Academic Emergency Medicine, vol. 17, Issue 4, Apr. 2, 2010, pp. 383-390.

Hou, et al., Viral infection triggers rapid differentiation of human blood monocytes into dendritic cells, *Blood*, Mar. 29, 2012, vol. 119, No. 12, pp. 3128-3132.

Lee, et al., "Mean cell vols. of neutrophils and monocytes are promising markers of sepsis in elderly patients", Blood Research, vol. 48, No. 3, Sep. 2013, 5 pages.

Levy, et al., "2001 SCCM/ESICM/ACCP/ATS/SIS Sepsis Definitions Conference", Critical Care Medicine, Mar. 28, 2003, 29: 530-538.

Liu, et al., "Hospital Deaths in Patients with Sepsis from 2 Independent Cohorts", *JAMA* Jul. 2, 2014; 312: 90-92.

Mardi, et al., Mean cell volume of neutrophils and monocytes compared with C-reactive protein, interleukin-6 and white blood cell count for prediction of sepsis and nonsystemic bacterial infections, accepted for publication, Sep. 23, 2009, International Journal of Laboratory Hematology 2010;32:410-418.

Park, et al., "Screening of sepsis using leukocyte cell population data from the Coulter automatic blood cell analyzer DxH800", International Journal of Laboratory Hematology, Dec. 6, 2010, 9 pages.

Raimondi, et al., "Automated Determination of Neutrophil Volume as Screening Test for Late-Onset Sepsis in Very Low Birth Infants", Pediatric Infectious Disease Journal, Feb. 2010;29:288-89.

Seymour, et al. "Severe Sepsis in Pre-Hospital Emergency Care: Analysis of Incidence, Care, and Outcome", American Journal of Respiratory Critical Care Medicine, Dec. 15, 2012; 186:1264-71.

Shalova, et al., "Human Monocytes Undergo Functional Reprogramming during Sepsis Mediated by Hypozia-Inducible Factor-1a", Immunity, Mar. 17, 2015; 42:484-98.

Skibsted, et al., "Bench-to-bedside review: Future novel diagnostics for sepsis—a systems biology approach", Critical Care Oct. 4, 2013;17:231, 15 pages.

Torio, et al., "National Inpatient Hospital Costs: The Most Expensive Conditions by Payer, 2011", H-CUP US, Aug. 2013, 8 pages, retrieved from: https://www.hcup-us.ahrq.gov/reports/statbriefs/sb160.jsp.

"UniCel DxH 800—Coulter Cellular Analysis System", Available online at: https://www.udh.med.sa/advices/DxH_operator_Manual.pdf, Aug. 5, 2017, 54 pages.

Vis, et al., "Verification and Quality Control of Routine Hematology Analyzers", International Journal of Laboratory Hematology, vol. 38, No. 1, May 9, 2016, pp. 100-109.

Kaukonen et al., "Systemic Inflammatory Response Syndrome Criteria in Defining Severe Sepsis," New England Journal of Medicine, 372: 1629-38, Apr. 23, 2015, (doi:610.1056/NEJMoal415236).

Singer et al., "The Third International Consensus Definitions for Sepsis and Septic Shock (Sepsis-3)," JAMA, 10 315(8): 801-810, Feb. 23, 2016, (doi: 10.1001/jama.2016.0287).

Goyette et al., "Hematologic changes in sepsis and their therapeutic implications," Seminars in Respiratory and Critical Care Medicine, vol. 25, No. 6, pp. 645-659 (2004).

Warner, "Tips for evaluating a peripheral blood smear for possible sepsis," Jan. 15, 2013, 3 pages, available at laboratorian.advanceweb.com/signs-of-sepsis/.

U.S. Appl. No. 16/073,757.

Beckman Coulter, Early Sepsis Indicator (ESId) Application for UniCel DxH 900 Series with System Manager Software, PN C26693AC (Jun. 2019), <https://www.beckmancoulter.corn/download/file/wsr-308328/C26693AC?type=pdf> (Year: 2019).

Beckman Coulter, Early Sepsis Indicator (ESId) Application Addendum, UniCel DxH 900 Series with System Manager Software Coulter Cellular Analysis System, PN C42014AC (Apr. 2020), <https://www.beckmancoulter.com/download/file/wsr-292218/C42014AC?type=pdf> (Year: 2020).

Beckman Coulter, UniCel DxH 900 Series with System Manager Software, PN B26647AG, <https://www.beckmancoulter.corn/download/file/wsr-156667/B26647AG?type=pdf> (Year: 2020).

Cembrowski, George S., B. Smith, and D. Tung. "Rationale for using insensitive quality control rules for today's hematology analyzers." *International Journal of Laboratory Hematology* 32.6p2 (2010): 606-615.

FDA 510(k) Substantial Equivalence Determination Decision Summary, 34 pages, <https://www.accessdata.fda.gov/cdrh_docs/reviews/K181599.pdf> (Year: 2018).

Chinese Office Action dated May 31, 2021, for Application No. 201780006733.8, 14 pages.

Chinese Office Action dated Mar. 9, 2022, for Application No. 201780006733.8, 4 pages.

European Examination Report dated Nov. 27, 2020, for Application No. 18712041.5, 11 pages.

European Examination Report dated Jul. 12, 2022, for Application No. 18845383.1, 13 pages.

Indian Office Action dated Jun. 25, 2021, for Application No. 201817031635, 7 pages.

Japanese Notification of Reasons for Refusal dated Feb. 4, 2022, for Application No. 2021-012832, 4 pages.

Japanese Notification of Reasons for Refusal dated Jun. 17, 2022, for Application No. 2021-012832, 2 pages.

Korean Office Action dated Aug. 27, 2021, for Application No. 10-2018-7024386, 27 pages.

U.S. Non-Final Rejection dated Jul. 9, 2021, for U.S. Appl. No. 15/987,541, 15 pages.

U.S. Final Rejection dated Feb. 17, 2022, for U.S. Appl. No. 15/987,541, 14 pages.

U.S. Notice of Allowance dated Sep. 1, 2022, for U.S. Appl. No. 15/987,541, 8 pages.

U.S. Restriction Requirement dated May 2, 2022, for U.S. Appl. No. 16/170,389, 7 pages.

U.S. Non-Final Rejection dated Aug. 1, 2022, for U.S. Appl. No. 16/170,389, 21 pages.

U.S. Restriction Requirement dated Mar. 14, 2022, for U.S. Appl. No. 16/390,597, 6 pages.

U.S. Non-Final Rejection dated Jun. 13, 2022, for U.S. Appl. No. 16/390,597, 8 pages.

U.S. Non-Final Rejection dated Jul. 2, 2021, for U.S. Appl. No. 16/390,633, 9 pages.

U.S. Non-Final Rejection dated Feb. 25, 2022, for U.S. Appl. No. 16/390,633, 13 pages.

U.S. Final Rejection dated Aug. 9, 2022, for U.S. Appl. No. 16/390,633, 11 pages.

U.S. Restriction Requirement dated Jun. 16, 2021, for U.S. Appl. No. 16/488,503, 8 pages.

U.S. Non-Final Rejection dated Nov. 24, 2021, for U.S. Appl. No. 16/488,503, 21 pages.

U.S. Final Rejection dated Aug. 11, 2022, for U.S. Appl. No. 16/488,503, 21 pages.

U.S. Non-Final Rejection dated Jun. 23, 2022, for U.S. Appl. No. 16/925,933, 9 pages.

U.S. Restriction Requirement dated Aug. 8, 2022, for U.S. Appl. No. 16/925,937, 13 pages.

* cited by examiner

TESTING AND REPRESENTING SUSPICION OF SEPSIS

CROSS-REFERENCES TO RELATED APPLICATIONS

This application is a continuation-in-part of U.S. patent application Ser. No. 15/987,541, filed May 23, 2018, entitled "CONDITION SPECIFIC SAMPLE ANALYSIS," the entire contents of which are herein incorporated by reference for all purposes. This application further claims the benefit of U.S. Provisional Patent Application No. 62/660,795, filed Apr. 20, 2018, entitled "SEPSIS INFECTION DETECTION SYSTEMS AND METHODS," which is hereby incorporated by reference in its entirety for all purposes.

FIELD

The disclosed technology pertains to analyzing samples, including using medical protocols and devices. Specific examples of the technology may indicate a suspicion of or likelihood of sepsis.

BACKGROUND

Often, when blood or another body fluid is analyzed, it may be subjected to tests to identify various parameters or biomarkers in a sample. However, it is possible that simply specifying parameters to be measured may provide suboptimal results in some cases. For example, in the context of health condition diagnosis and treatment, it is possible that a single parameter may be relevant to the treatment and/or diagnosis of multiple conditions, including some conditions that would benefit from measurements having a level of accuracy that would be pointless for other conditions. Additionally, in some cases, tests may be organized, and test results may be reported based on particular types of parameters (e.g., cell types), but it is possible that a sample may be collected and/or analyzed for a purpose that would benefit from consideration of information related to multiple types of parameters. This can cause various problems, such as making it more difficult to obtain information relevant to a particular analytic goal and/or rendering analysis less efficient in cases where tests for a parameter are keyed to more demanding requirements than may be appropriate for a particular use.

Sepsis is an uncontrolled systemic inflammatory response to infection that may rapidly progress to a life-threatening condition that can lead to shock and organ failure (i.e., septic shock and severe sepsis) if not treated immediately. A patient admitted to a medical facility may show clinical features of systemic inflammation. A medical professional may then attempt to determine if the inflammation is caused by an infection, leading to a diagnosis of sepsis, or some other causes, leading to a diagnosis of systemic inflammatory response syndrome (SIRS). In some cases, a patient may have no obvious signs of systemic inflammation, which may mean that the patient may not be considered at risk for sepsis. For example, patients who are younger and healthier may compensate for having sepsis and may show no signs or inconsistent signs of sepsis or inflammation and, therefore, may not be treated for sepsis and suffer consequences of sepsis being untreated.

If undetected, sepsis may lead to severe sepsis or septic shock, which has a mortality rate of about 60%. A large fraction of hospital deaths are associated with sepsis. Diagnosing sepsis is challenging because of the lack of an accurate biomarker. Additionally, clinical criteria that may indicate sepsis, such as hypothermia, hyperthermia, tachycardia, tachypnea, may not distinguish sepsis from SIRS or other conditions. These criteria may be associated with non-infectious etiologies that may be present in a hospital emergency room, including trauma, burns, pancreatitis, sickle cell crisis, and other inflammatory disorders. These similarities between sepsis and inflammation may make diagnosing sepsis challenging and time-consuming. For example, obtaining blood culture results to confirm an infection and/or identify a pathogen responsible for the infection may take several days. During the time it takes to complete conventional diagnostic testing, the patient's condition could deteriorate, possibly to a degree that the patient requires extraordinary clinical support or can no longer be treated effectively. For these and additional reasons, improved or new systems and methods for assessing the likelihood of systemic infection, including sepsis, are desired.

BRIEF SUMMARY

There is a need for improved technology for analyzing samples in a manner that is consistent with specific analytic goals. It may thus be an object of some embodiments to provide a method that could comprise steps such as receiving an order identifying a condition that one or more tests should be performed, determining the one or more tests to perform to diagnose or assess the condition, determining a set of custom behaviors to use in performing that test and obtaining a result for that test by performing it using the custom behaviors, and presenting the results for the one or more tests performed to diagnoses or assess the condition. In some embodiments, this objective may be fulfilled by the subject matter of the independent claims, wherein further embodiments are incorporated in the dependent claims.

Embodiments of the present disclosure may allow for an efficient and accurate way to assess whether an individual has sepsis or may develop sepsis or a severe infection.

Embodiments of the present invention improve upon diagnostic, biological, and medical related technologies or technical fields by providing a fast, simple, and accurate determination of the sepsis status. Based on the sepsis status, treatment may be started quickly, thereby preventing complications, including organ failure and death, of not treating sepsis fast enough. The sepsis status may include an indication that the patient is at high risk of developing sepsis, rather than a diagnosis of sepsis.

The sepsis status may indicate sepsis is indicated by the blood sample or that sepsis is likely to develop based on characteristics measured in the blood sample. Sepsis being likely in the blood sample may indicate that a treatment for sepsis in the individual is recommended or needed. Sepsis results from an uncontrolled systemic response to an infection. Sepsis may result from any infection in the body. For example, a simple skin infection may trigger a septic event. A post-surgical infection may lead to sepsis as the post-surgical infection may include infection and systemic inflammation. Predicting which infections may result in a septic event is difficult and not always possible. Clinicians desire an early detection or indication that a patient may become septic.

Embodiments of the present technology include a method for testing a blood sample for sepsis. The method may include receiving a blood sample from an individual. The method may also include executing an instruction to analyze the blood sample for characteristics related to sepsis. In addition, the method may include measuring values of a set of characteristics in the blood sample. The set of characteristics may be determined prior to measuring the values. The method may further include analyzing the values of the set of characteristics to produce a representation of a suspicion of sepsis. In addition, the method may include displaying the representation.

Embodiments of the present technology include a method of training and using machine learning models to estimate a likelihood of sepsis based on test blood sample data sets. The method may include receiving, by a computer system, a training data set including a plurality of data elements. Each training data element of the plurality of data elements may include a blood sample data set and a condition data set. The blood sample data set may include, for each individual of a plurality of individuals, values for a set of characteristics associated with a blood sample. The condition data set may indicate a presence of sepsis in each individual of the plurality of individuals. The method may also include training a machine learning model, using the training data set. The training may result in identifying one or more parameters of a function in the machine learning model based on correspondences between the blood sample data set and the condition data set. Furthermore, the method may include receiving, by the computer system, a test blood sample data set including a value for each characteristic of the set of characteristics. The method may use the trained machine learning model and the test blood sample data set to generate a representation of the likelihood of sepsis in the test blood sample data set.

Embodiments of the present technology may include an automated system for testing a blood sample for sepsis. The blood sample may be obtained from an individual. The system may include a first module. The first module may include a first assembly configured to measure direct current (DC) impedance of cells of the blood sample passing individually through a cell interrogation zone. The first module may also include a second assembly configured to measure radiofrequency (RF) conductivity of cells of the blood sample passing individually through the cell interrogation zone. The first module may further include a third assembly configured to measure light propagation of cells of the blood sample passing individually through the cell interrogation zone. In addition, the automated system may include a second module configured to count cells. The automated system may also include a data processing module in connectivity with the first module and the second module. The data processing module may include a processor and a tangible, non-transitory computer readable medium, the tangible non-transitory computer readable medium programmed with a computer application. The computer application when executed by a processor may cause the processor to execute an instruction to analyze the blood sample for sepsis. The processor may be caused to measure values of a set of characteristics in the blood sample. The set of characteristics may be determined prior to measuring the values. The processor may also be caused to analyze the values of the set of characteristics to produce a representation of a suspicion of sepsis. The processor may further be caused to display the representation.

A better understanding of the nature and advantages of embodiments of the present invention may be gained with reference to the following detailed description and the accompanying drawings.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

Figure 1:
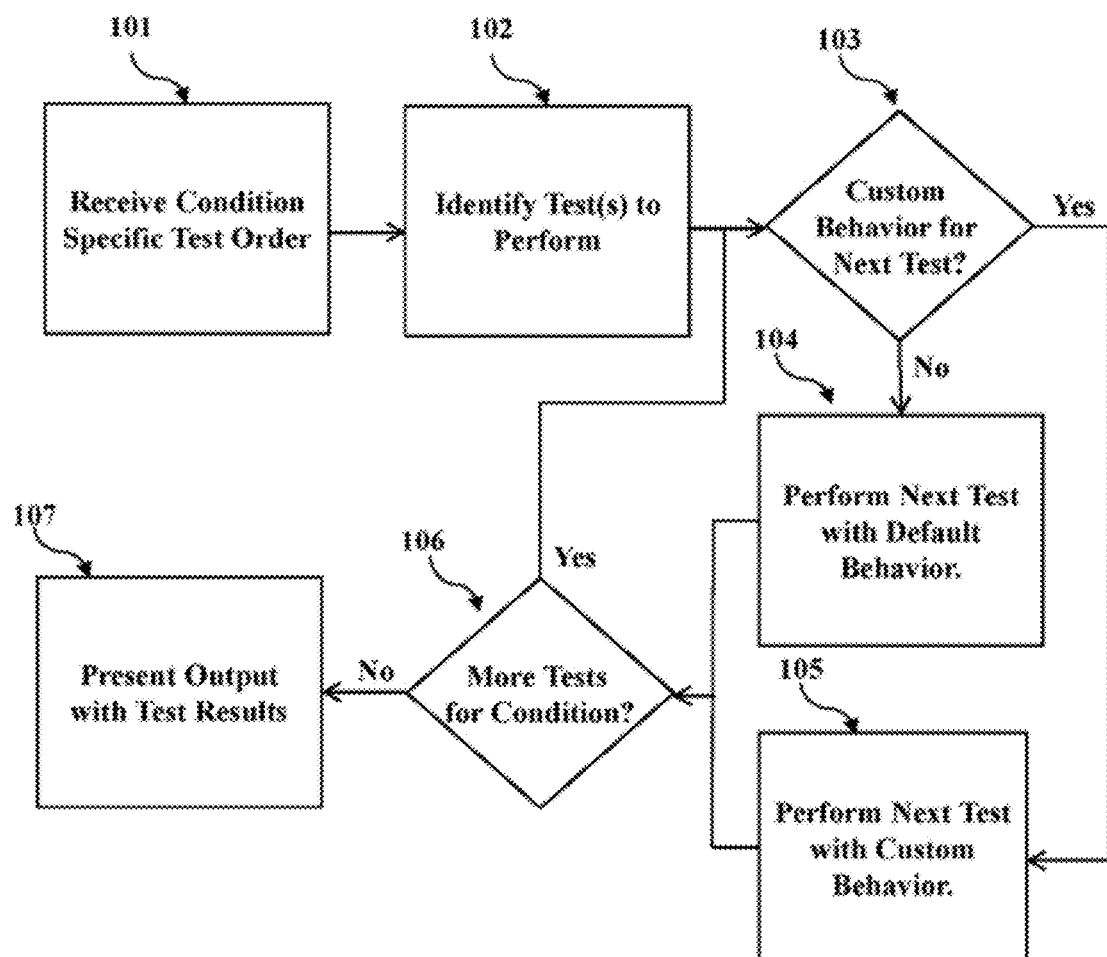
FIG. 1 presents an exemplary process that may be used in some embodiments to control and/or present results of tests on a condition specific basis.

Diagnostic markers for sepsis have been researched for many years. Even so, there has not been a clear diagnostic test or biomarker for determining sepsis available. It was previously believed that a series of seven blood-cell-related factors could be reviewed in order to determine possible septic infection. See, for example, Park et al., "Screening of sepsis using leukocyte cell population data from the Coulter automatic blood cell analyzer DxH800," *International Journal of Laboratory Hematology*, 2011, 33, 391-399 at 397-98. As recently as a few years ago, it was believed that parameters or indices based on a calculation including at least two of the seven factors were needed in order to make a septic infection prediction. Standard deviation of monocyte volume, and white blood cell count are parameters that have been related to the likelihood of sepsis. While these and other parameters have shown predictive ability for sepsis, other parameters or other combination of parameters (including the mentioned parameters) may also be informative in determining a likelihood of sepsis. In addition, even with identified parameters, the values of the parameters may vary with the particular patient population, sample collection practices, medical facilities, and medical devices. Methods and apparatuses that can account for variations may also be desired.

As used herein, "parameter" may refer to a property measured from a blood sample (e.g., cell population data parameters) or independent variables in a function. The broader definition of "parameter" including both types applies unless context makes clear otherwise. A "characteristic" refers to a property of a blood sample and not an independent variable in a function.

The definition of sepsis itself has changed, illustrating additional difficulties in conclusively diagnosing sepsis. Under the Sepsis-2 definition, sepsis was defined based on systemic inflammatory response syndrome (SIRS) criteria. SIRS may refer to a clinical syndrome that results from a dysregulated inflammatory response to a noninfectious insult, such as an autoimmune disorder, pancreatitis, vasculitis, thromboembolism, burns, or surgery. SIRS criteria include temperature, heart rate, respiratory rate, and white blood cell count. SIRS criteria are described in Kaukonen et al., "Systemic Inflammatory Response Syndrome Criteria in Defining Severe Sepsis," *New England of Med.*, 372:1629-

38 (2015) (doi: 10.1056/NEJMoa1415236) and the Supplementary Appendix, the contents of both of which are incorporated herein by reference for all purposes. "Sepsis" may be the clinical syndrome that results from a dysregulated inflammatory response to an infection. Under Sepsis-2, sepsis includes two SIRS criteria and infection. "Severe sepsis" may refer to sepsis-induced tissue hypoperfusion or organ dysfunction resulting from infection. "Septic shock" may refer to a condition of severe sepsis plus hypotension persisting despite adequate fluid resuscitation, which may be defined as infusion of 20-30 mL/kg of crystalloids.

In 2016, Sepsis-3 updated the definition of sepsis, which is described in Singer et al., "The Third International Consensus Definitions for Sepsis and Septic Shock (Sepsis-3)," JAMA, 315(8):801-810 (2016) (doi: 10.1001/jama.2016.0287). Sepsis-3 defines sepsis as a life-threatening organ dysfunction caused by a dysregulated host response to infection. Organ dysfunction can be identified using a Sequential [Sepsis-related] Organ Failure Assessment (SOFA) score. The SOFA "score grades abnormality by organ system and accounts for clinical interventions." "Septic shock" is considered a subset of sepsis, when "underlying circulatory and cellular/metabolic abnormalities are profound enough to substantially increase mortality." There is no "severe sepsis" in Sepsis-3. As Sepsis-2 and Sepsis-3 definitions are not identical, even defining "sepsis" is challenging. Nonetheless, certain patient sample measurements, alone or in combination, may identify patients who meet the criteria for Sepsis-2 and/or Sepsis-3, or are at elevated risk of meeting the criteria for Sepsis-2 and/or Sepsis-3 in the near future (e.g., within 24 hours, or within 48 hours, of sample testing), as described herein.

As sepsis is defined based on a set of clinical signs and symptoms, sepsis is not detectable in the blood the way a parasite or a low hemoglobin concentration may be detected. Methods and systems described herein may enable a clinician to identify or determine sepsis when clinical conditions are vague or non-specific (e.g., flu-like symptoms, which may be symptoms of sepsis). If "detecting" or a form of the word is used herein with sepsis, the term should be understood to mean determining, diagnosing, or assessing sepsis, rather than measuring a specific component definitively indicating sepsis.

Conventional systems and methods for diagnosing sepsis may be inefficient and/or time consuming. In current practice, clinical criteria may be used to diagnose sepsis by detecting systemic inflammation that accompanies sepsis. The clinical criteria, however, may be common to both sepsis and SIRS, which may be associated with non-infectious conditions. An individual who may have sepsis may undergo laboratory tests, including but not limited to a test to generate a complete blood count (CBC) with differential (CBC-diff); measurements of C-reactive protein (CRP), serum lactate, erythrocyte sedimentation rate (ESR), and Procalcitonin (PCT); and cultures for bacteria. These technologies may result in poor sensitivity and/or specificity when used to diagnose sepsis. Other systems and methods may be limited to leukocyte Cell Population Data (CPD) and may still be lacking in sensitivity and/or specificity. Some conventional methods may use CPD parameter(s) (e.g., monocyte volume) that lack the sensitivity and/or specificity of CPD parameters used herein. In some cases, conventional methods may require the use of multiple analytical methods to show an increased sensitivity or specificity. Some of these tests may be expensive and may not be run routinely on individuals, and as a result, individuals who are infected and potentially septic but not yet symptomatic may not be diagnosed promptly or not diagnosed at all. The lack of an efficient and accurate method and system to evaluate the infection status may lead to a clinician administering antibiotics as a precautionary measure, resulting in overuse of antibiotics. Adverse drug events, adverse treatment interactions or side effects that might be easily managed in a healthy patient can present significant problems in a patient with SIRS, sepsis or similarly severe clinical conditions. Medicating all potentially septic patients with antibiotics, therefore, is not an ideal clinical strategy.

On the other hand, waiting for test results may endanger an individual's life. Analyzing a blood culture to definitively diagnose sepsis may take two to four days. In that time, an individual can develop sepsis, develop organ failure, be past the point of recovery, and eventually die. A quick and accurate method to evaluate sepsis would improve patient outcomes and save lives. Any time saved in identifying sepsis or potential sepsis may improve patient outcomes. By one estimate, a septic patient's chance of recovery decreases by 7%-8% for every hour of delay in treatment of the underlying infection.

Other tests may also be inadequate. CRP may not be specific to bacterial and viral infections, as it has also been associated with cancer and heart disease. Serum lactate may not be specific to sepsis and may be used more as a prognostic biomarker in sepsis instead of a diagnostic biomarker. ESR may represent physical properties associated with inflammatory processes but has poor specificity for infection. Blood cultures may be too time consuming to allow physicians to make immediate or timely treatment decisions. Additionally, antibiotic drugs and/or fastidious pathogens may limit the sensitivity of blood cultures. PCT, lacking sufficient sensitivity and specificity in symptomatic patients, may not reliably differentiate sepsis from other non-infectious causes of SIRS in critically ill patients. Furthermore, because PCT may be a separate, specialized test that may be performed only upon clinician request, the test may not be administered early and may not be an early identifier of septic patients.

Conventional systems may include computers, which are not able to evaluate the infection status with sufficient sensitivity and specificity even if the computer had all the information provided from a blood sample. In some instances, one or more conventional tests for sepsis may indicate sepsis, and one or more conventional tests for sepsis may be inconclusive or contraindicate sepsis. Conventional systems may be unable to reconcile inconsistent or conflicting indicators with regard to whether a patient has or is likely to develop sepsis. Embodiments of the present invention may improve computer-related technology by allowing the computer to perform evaluation of the infection status, including the evaluation of a sepsis status, which may include a suspicion or likelihood of sepsis.

Embodiments of the present invention may evaluate the sepsis status. The sepsis status may indicate that an individual has sepsis, a suspicion of sepsis, or a likelihood of sepsis. If an individual is evaluated to have sepsis, suspected to have sepsis, or likely to have sepsis, clinical criteria may be used to confirm whether the individual has sepsis. Clinical criteria may include heart rate, body temperature, presence of a fever, and mental status. Individuals diagnosed with sepsis may receive closer monitoring, hospital admission, aggressive IV fluids, repeated blood cultures, vitamin (e.g. vitamin C) treatment, antibiotic treatment, antiviral treatment, antifungal treatment, supportive care, and/or prioritized diagnoses and treatment.

I. Panels for Detecting Conditions

In light of the above, it could be beneficial to be able to automatically customize the analysis of samples based on specific objectives that analysis is intended to or could be expected to advance. According to a first aspect, some embodiments may include a method comprising steps such as receiving an order identifying a condition that one or more tests should be performed to detect, determining the one or more tests to perform to detect the condition, determining a set of custom behaviors to use in performing that test and obtaining a result for that test by performing it using the custom behaviors, and presenting the results for the one or more tests performed to detect the condition.

In some embodiments according to the first aspect, the one or more tests to perform to detect the condition may include a first test in a first panel and a second test in a second panel. In such embodiments, the results for the one or more tests performed to detect the condition may be simultaneously presented in a single output.

In some embodiments according to the first aspect, there may be a first test to perform to detect the condition that is performed on an analyzer having a default data collection requirement, and the set of custom behaviors may comprise a custom data requirement for the first test. In some embodiments of this type, the condition may be a condition that needs to be detected at an early state, for example in a certain embodiment this may be sepsis, the default data collection requirement for the first test may be acquiring data from between 500 and 1,000 monocytes, and the extended data collection requirement for the second test may be acquiring data from a higher number of monocytes (e.g., between 1,000 and 2,000, between 4,000 and 5,000, etc.). Additionally, in other embodiments, various other parameters may be used to detect a condition at an early state or even before a condition can be identified based on clinical signs and symptoms from a physical examination. Similarly, in some embodiments such as described initially in this paragraph, the one or more tests to perform to detect the condition may comprise a second test, and the set of custom behaviors to use in performing the second test may be no custom behaviors. The different tests may involve analyzing the same or similar features in different ways or at different times, e.g., acquiring data from additional cells to increase the confidence in an observation or measurement or to evaluate a change over time. The different tests may involve analyzing different features, e.g., a distribution width for a cell population or cell sub-population, or one or more extrema for a cell population or cell sub-population. The different tests may involve analyzing a mix of the same features and different features, so long as the "different tests" are not the same test performed at what is clinically the same time, i.e., over a time period in which no difference in the test result would be expected based on actual differences in the patient sample as compared to normal sample-to-sample or test-to-test variability.

In some embodiments according to the first aspect, the method may comprise, using an index calculation function, calculating a value indicating a likelihood that the condition identified in the order is present. Such an embodiment may also comprise presenting the value indicating the likelihood that the condition identified in the order is present. Similarly, in some embodiments of this type, the index calculation function for a condition identified in an order may be a function that calculates a value indicating the likelihood that the condition is present based on a predefined set of parameters. In some embodiments, parameters may, but are not limited to, distribution width associated with various measurable parameters associated with the patient sample; ratios between various measurable parameters associated with the patient sample; cell population data associated with granulated cells or a sub-population of granulated cells in a blood sample; cell population data associated with lymphocytes or monocytes in a blood sample; the standard deviation of the volume of monocytes in the patient sample; a count of white blood cells in the patient sample; a sum of monocytes and neutrophils in the patient sample; WBC' (a linear transformation of the count of white blood cells in the patient sample, as is described below); the standard deviation of the volume of monocytes in the patient sample following an extended data range (volume) mode from a higher number of monocytes than normal; a count of early granulated cells in the patient sample; a count of neutrophils in the patient sample; one or more measures of the neutrophil cell population or features of the neutrophils in the patient samples, such as average volume, standard deviation of volume, or the like; a combination of the standard deviation of the volume of the monocytes in the patient sample, with or without extended data range (volume) mode, and a count of white blood cells in the patient sample; a combination of the standard deviation of the volume of the monocytes in the patient sample, with or without extended data range (volume) mode, and a sum of monocytes and neutrophils in the patient sample; a combination of the standard deviation of the volume of the monocytes in the patient sample, with or without extended data range (volume) mode, and WBC'; a combination of a count of white blood cells in the patient sample and a sum of monocytes and neutrophils in the patient sample; a combination of a count of white blood cells in the patient sample and the standard deviation of the volume of the monocytes in the patient sample, with or without extended data range (volume) mode; a combination of a ratio of monocytes to neutrophils in the patient sample and WBC'; a combination of the standard deviation of the volume of the monocytes in the patient sample, with or without extended data range (volume) mode, a count of white blood cells in the patient sample, and a ratio of monocytes to neutrophils in the patient sample; a combination of the standard deviation of the volume of the monocytes in the patient sample, with or without extended data range (volume) mode, WBC', and a ratio of monocytes to neutrophils in the patient sample; and combinations and sub-combinations thereof. Extended data range (volume) mode refers to using an extended volume range that allows monocyte populations with cell volumes that exceed the five-part differential measuring range to be fully developed so that a standard deviation of the volume of the monocytes can be computed based on the full monocyte population.

Combinations of parameters may be assessed sequentially, e.g., evaluating an observation from the patient sample to a threshold for suspicion of sepsis for a first parameter, and then evaluating an observation from the patient sample to a threshold for suspicion of sepsis for a second parameter; or may be assessed as a co-variate regression; or may be assessed as an index or transformation; or a combination of means of combining the parameters may be used. In some instances, including, but not limited to, white blood cell count, a transformation may be used to consider both a lower threshold and an upper threshold simultaneously. In other instances, a transformation may be used to moderate large differences in absolute value between two parameters or to remove or reduce the influence of correlated parameters (e.g., a parameter influenced by cell volume [e.g., RF] may be divided by volume to remove that factor). Any value from negative infinity to positive infinity may be transformed to a [0,1] range. Exemplary transformations may be linear or non-linear, including logarithmic transformations. A computer performing the method may be communicatively connected to a remotely located server and may also be configured to receive an updated index calculation function.

In some embodiments according to the first aspect, the one or more tests to perform to detect the condition may comprise a first test and a second test, where the first test is a test of a white blood cell parameter and the second test may be a test of a red blood cell parameter. Additionally, in some embodiments of this type the first test and the second test may be performed using reagents as part of a single panel or in a single apparatus.

Corresponding systems comprising one or more computers configured by computer executable instructions stored on non-transitory computer readable media to perform steps of methods described in any of the preceding embodiments, as well as non-transitory computer readable media storing instructions for performing steps of method described in any of the preceding embodiments, could also be implemented without undue experimentation by those of ordinary skill in the art based on this disclosure. Similarly, the disclosed technology may be used in the diagnosis of a variety of clinical conditions, such as sepsis, malaria, dengue, anemia, leukemia, etc. Accordingly, the preceding description of potential embodiments and aspects, as well as the discussion of illustrative embodiments set forth herein, should be understood as being illustrative only, and should not be treated as limiting.

Turning now to FIG. 1, FIG. 1 presents an exemplary process that may be used in some embodiments to control and/or present results of tests on a condition specific basis. Initially, in the process of FIG. 1, an order will be received 101 for testing for a specific condition. Preferably, this step (as well, optionally, as the other steps from the process of FIG. 1) will be performed by a computer controlling a piece of laboratory equipment (e.g., a hematology analyzer) that would perform tests for detecting the relevant condition. In embodiments where a process such as illustrated in FIG. 1 is performed by a computer, the step of receiving 101 a condition specific test order could be performed in a variety of manners. For example, in some embodiments, a computer may be configured to receive 101 an order for testing for a specific condition when a physician specifies that tests for that condition should be run on a sample. Such an order may, in some embodiments, be transmitted electronically to the analyzer, while in other embodiments an analyzer implemented based on this disclosure may be configured to include specific conditions in a menu presented to an operator and to allow that operator to use that menu to specify the condition. In yet other embodiments, a computer may be configured to automatically generate an order to test a sample for a condition. For example, the computer may be configured with rules (such as those described in co-pending PCT application PCT/US18/20087 for a Cross Discipline Disease Management System, the disclosure of which is hereby incorporated by reference in its entirety) for triggering a reflex test for a specific condition when it appears that there is a heightened likelihood that that condition is present.

In this context, a "reflex test" refers to a test that is performed because certain data or circumstances indicate that additional testing would be helpful. Reflex testing often occurs because of improbable or unusual results (e.g., very high cell counts, potentially indicative of a miscount rather than actual cell density in a sample or a statistically aberrant test result for a sample), or results which could have significant clinical effects (e.g., platelet counts that would disqualify a patient for surgery). In such cases, the reflex testing may be intended to verify an improbable or clinically important test result. In the context of this disclosure, reflex testing may occur to confirm a result, to increase the confidence in a result (e.g., by extended sampling), and/or because the result of one or more routine or specially-ordered tests may indicate that another panel of tests, such as a panel of tests for a specific condition, such as sepsis, is indicated. The reflex testing may occur because a medical practitioner ordered a condition-specific panel, and a set of one or more primary tests indicated that additional testing was advisable (e.g., one or more results was consistent with a diagnosis of the condition). The reflex testing for a condition-specific panel may occur even if the medical practitioner did not order a condition-specific panel, if the results indicate that the condition-specific panel should be tested. Alternately, the testing described herein as reflex testing may be part of the routine processing of a condition-specific panel (e.g., not actually reflex testing, but rather routine testing vis-à-vis an order for a condition-specific panel, regardless of the results of whatever tests happen to be run first in time).

Exemplary circumstances that could trigger reflex testing for a condition-specific panel include patient demographics and/or patient condition (e.g., a sepsis-specific panel could be run for all emergency department patients with a fever or altered mental state, based on information in the test order and/or the hospital information systems, including electronic medical records and/or the laboratory information system); the result of whatever test or tests for a particular sample were ordered (e.g., a sepsis-specific panel might be run for any sample submitted for a complete blood count with differential or CBC-diff with a high standard of deviation for monocyte volume); the order of a medical practitioner (e.g., an order to complete a condition-specific panel); the initial findings from a condition-specific panel (e.g., additional testing run as part of a condition-specific panel only if certain primary tests are consistent with diagnosis of the condition, for example, testing a blood sample from a patient with suspected sepsis for WBC' and standard deviation of monocyte volume, and performing extended testing for other parameters only if one or both tests exceed cutoff values for suspicion of sepsis); or combinations thereof. For example, in some embodiments, a computer may be configured to be able to receive 101 an order for testing a specific condition both when it is directly requested by a physician, and when it is automatically generated.

In the process of FIG. 1, once a condition specific test order has been received 101, the process continues with identifying 102 the test(s) to perform for that condition. As with receiving 101 the condition specific test order, the step of identifying 102 test(s) for the specified condition may be performed in a variety of different ways. For example, in some embodiments, a computer performing a method such as shown in FIG. 1 may have stored, either in its own memory or in a local database, data (e.g., in one or more tables) correlating particular conditions with particular test(s) that would be relevant to the identification of those conditions. In such an embodiment, the step of identifying 102 the test(s) to perform may be done by the computer retrieving the test(s) from its own memory or local database by running a query using the condition specified in the previously received 101 order. In other embodiments, a computer performing a process such as shown in FIG. 1 may query a remote database (e.g., a database hosted on a cloud server) to identify 102 what test(s) should be performed, or may attempt to query a remote database and, if such a query fails (e.g., if there is a problem communicating with the remote database) fall back on whatever information is stored in the computer's memory or in a local database.

Other alternatives may also be possible. For example, in some embodiments, a condition specific test order may specify both the test(s) to perform and the condition which the test(s) are intended to detect. In this type of scenario, a computer performing a process such as shown in FIG. 1 may simply identify 102 the test(s) to perform as the test(s) specified in the order itself, or may identify 102 the test(s) as the test(s) specified in the order plus any additional test(s) that may be indicated by information stored in a local or remote database. Additional variations (e.g., identifying test(s) specified in an order as the test(s) to be performed, with any additional test(s) indicated by information in a local or remote database being treated as possible reflex test(s) in case the test(s) specified in the order were inconclusive or indicated that additional tests may be clinically relevant) may also be possible in some embodiments. Accordingly, the discussion above of identifying 102 test(s) to be performed, like the discussion of receiving 101 a condition specific test order, should be understood as being illustrative only, and should not be treated as limiting on the scope of any claims in this document or any other document claiming the benefit of this disclosure.

The database may be absolute, applying the same standard to all condition-specific test orders. In other cases, the database may be modified based, for example, on local data trends, temporal data trends, local decision rules, patient subpopulations, or the like. For example, an oncology practice may include different tests, different thresholds for triggering reflex testing, or may use different formulas to assess the likelihood of sepsis than an emergency department, an intensive care unit, a post-operative observation unit, a pediatric unit, etc.

After identification 102 of the test(s) to be performed, the process of FIG. 1 continues with a determination 103 of whether there are custom behaviors for the next test (which, if this is the first time the determination 103 had been performed for a sample, would be the first test identified for the condition). To illustrate what this type of determination might entail, consider the case where the received 101 order is to test a sample to determine whether the individual from whom that sample was collected is suffering from sepsis, and the identified 102 test(s) to perform on that sample included determining monocyte distribution width (MDW). Consider also the hypothetical situation in which such an order is to be processed using an instrument having a default behavior for determining MDW that includes a number of monocytes to detect in a sample. In this type of hypothetical scenario, the step of determining 103 whether there is custom behavior for the sample may include determining that, because the sample is being run to diagnose sepsis, the data collection should be extended such that the default behavior would be overridden and data for a larger number of monocytes would be acquired, thereby allowing for a more precise MDW determination of a type that may be appropriate for testing for sepsis but that may not be necessary for other purposes.

In some embodiments following this type of hypothetical scenario, the default behavior for determining MDW may be detection of between 500 and 1,000 monocytes, while the custom behavior may be acquiring data for between 1,000 and 2,000 monocytes. In other embodiments, the custom behavior may be acquiring data for between 4,000 and 5,000 monocytes. In other embodiments, different types of custom behaviors may be implemented. For example, the sample may be reflexed for additional testing on the same or different apparatus. As described above, exemplary reflex testing may include other cell population measurements. However, reflex testing could also include testing on different apparatuses and/or in different fields. For example, a patient sample could be reflexed between a cell counting and/or measuring apparatus and one or more of a chemical, immunoassay, microbiological, or other apparatus to supplement or complete the initial order. Accordingly, the discussion above of specific custom behaviors should be understood as being illustrative only, and should not be treated as limiting.

With respect to execution, the determination 103 of whether there are custom behaviors for a test could be performed in manners similar to those discussed previously for the identification 102 of tests to perform. Thus, in some embodiments, whether there is custom behavior for a test could be determined 103 by a computer performing a query of its own memory of a local database using the relevant test and condition, and use the result of that query to define the custom behavior (if any) for that test. Similarly, in some embodiments, whether there is custom behavior for a test could be determined 103 by querying a remote database and/or by reference to the condition specific testing order (e.g., if the order had specified particular behaviors, such as extended data collection, to be used when performing particular test(s)). Accordingly, like the identification 102 of test(s), the determination 103 of custom behavior should be understood as potentially being susceptible to implementation in different manners, and the protection provided by this or any related document should not be limited to only embodiments in which that step is performed using one of the exemplary implementations described herein.

After the determination 103 had been made of whether there were custom behaviors for a test, that test could then be performed 104 with its default behaviors (if there were no custom behaviors for that test), or could be performed 105 with the custom behaviors (if it had been determined 103 that such custom behaviors existed). This could then repeat until all tests for the condition 106 from the condition specific test order had been performed. Alternately, or additionally, the custom behavior could relate to how the test results are acquired. For example, different population characteristics, such as extrema or standard deviations, may be identified; ratios or relative measures of different cells, cell population characteristics, biomarkers, or the like may be calculated; or different thresholds for declaring a sample normal or abnormal may be applied as custom behaviors. In some cases, the custom behaviors may include if-then cascades that effect how the data is analyzed or represented to a human. In some cases, an if-then cascade may include reflex testing, or cycles between data analysis and reflex testing, until a reasonably reliable recommendation regarding a condition-specific diagnosis can be made or the cascade is terminated, e.g., because the analysis is indeterminate or the sample has been spent or expired and cannot be subjected to further testing. The resolution of the data acquired may be increased or decreased based on the data analysis. If less precision or faster data processing is preferred, then the resolution of the data as it is acquired may be decreased. If greater precision is desired, then the resolution of the data as it is acquired may be increased.

Finally, the results of the tests could be presented 107. In some embodiments, this may be done, for example, by simply presenting the test results on a panel by panel basis and allowing the user to see the test results by selecting the panels in which the tests were contained. Alternatively, in some embodiments, all test results may be gathered into a single page so that they could be presented together regardless of whether the reagents for those tests had been included in different panels. For instance, in this type of embodiment, if tests performed on a sample had included a test performed with a reagent from a white blood cell panel and a test with a reagent from a red blood cell panel, then those results could be presented 107 together in a single interface despite the fact that the tests had been in (i.e., had relied on reagents or different test processes from) different panels. Additionally, some embodiments of aspects of the disclosed technology may allow analyzers that do not include code for gathering results of tests from multiple panels in a single output to provide condition-specific, unified output through the use of condition specific panels. That is, in some embodiments a panel may be provided which is organized to include the test results that would be used to detect a particular condition, rather than to include test results on a particular type of subject matter (e.g., red blood cell or white blood cell panels).

Further variations on the presentation 107 of results may also be possible in some embodiments. For example, in some embodiments, prior to the presentation of results, the data gathered in the tests may be used to calculate a value reflecting how likely it is that the specified condition is present. This may be calculated, in some embodiments, using an equation of the general form index=f(parameter 1, parameter 2, . . . parameter n) to calculate a value illustrating the likelihood that a patient from whom a sample was taken has the relevant clinical condition based on the data collected regarding that sample. In some cases, this likelihood may be determined without reference to a single, condition-specific biomarker or analyte. For example, the condition may be sepsis, for which there is no known biomarker or analyte that is individually diagnostic of sepsis, in contrast to a condition like infection with *E. coli*, which can be confirmed by blood culture.

In some embodiments, the index presentation may include identification of additional tests that might facilitate a diagnosis. For example, if the system is unable to reflex test between laboratory instruments of different types, the index presentation may include specific chemical, immunoassay, microbiological or cell measurement tests that might improve the accuracy or precision of the index, based on which test(s) were unavailable for reflex testing and/or were not included in the medical practitioner's order.

In some embodiments, a computer in a laboratory that would perform an index calculation such as described above may be configured to communicate with a remote server to determine if the server had a model for calculating an index that was more recent than the computer's then current model and, if so, the computer could update to use the more current model for future index calculations. In embodiments where this type of updating is supported, it may also be used for upgrading data other than models used for calculating likelihood indices. For example, it is possible that, as additional research is done, a remote server may be updated to include data indicating new tests and/or custom behaviors that had been found to be useful in detecting various conditions, and this information may be propagated to local laboratory computers in a manner similar to that described for the index updates.

II. Panels for Determining Sepsis

Embodiments of the present technology include panels for testing for sepsis. The panel may be run on blood samples commonly obtained from patients visiting an emergency department. Testing for sepsis may or may not include diagnosing sepsis. In some embodiments, the results of a panel for sepsis may indicate that the possibility of sepsis is a concern for the individual and may need further analysis or monitoring, without stating that sepsis is present in the individual. The medical practitioner may then decide, based on the results of the panel, to run additional tests or to proactively start treatment for sepsis. In some cases, the individual may not show any obvious symptoms of sepsis, and the result of the panel may bring the possibility of sepsis to a medical practitioner's attention. For example, an individual admitted to an emergency department may be young (e.g., ages 18-29) and not show any symptoms of sepsis or may present with non-specific complaints, and the panel may indicate sepsis is a concern for the individual.

The panels include components or methods, including measurement devices or techniques, that generate new data. Measurement devices are described below. Measurement techniques include analyzing blood cell parameter data (e.g., leukocyte cell population data (CPD)) in a new way. Conventional panels of analyzing blood cell parameter data do not generate data that is specific for determining sepsis or assessing a suspicion of sepsis or a likelihood of sepsis, and do not analyze or present the data to draw attention to the possibility of sepsis, even if the results indicate a high probability of sepsis.

A suspicion of sepsis is a categorization that sepsis is suspected or cause for concern in a patient. A likelihood of sepsis is a probability that the patient is septic. Sepsis may be suspected in a patient based on physical examination, but not likely in the patient. Conversely, a patient may be septic or may be at high risk of developing sepsis even though sepsis is not suspected based on physical examination. Suspicion of sepsis may be categorized in binary terms—either yes or no; sepsis is suspected or it is not. Suspicion of sepsis may then lead to additional tests that may determine the likelihood of sepsis. However, in some embodiments, suspicion may be scaled to the likelihood of sepsis, with a higher likelihood associated with a higher value.

A. Example Method

Figure 2:
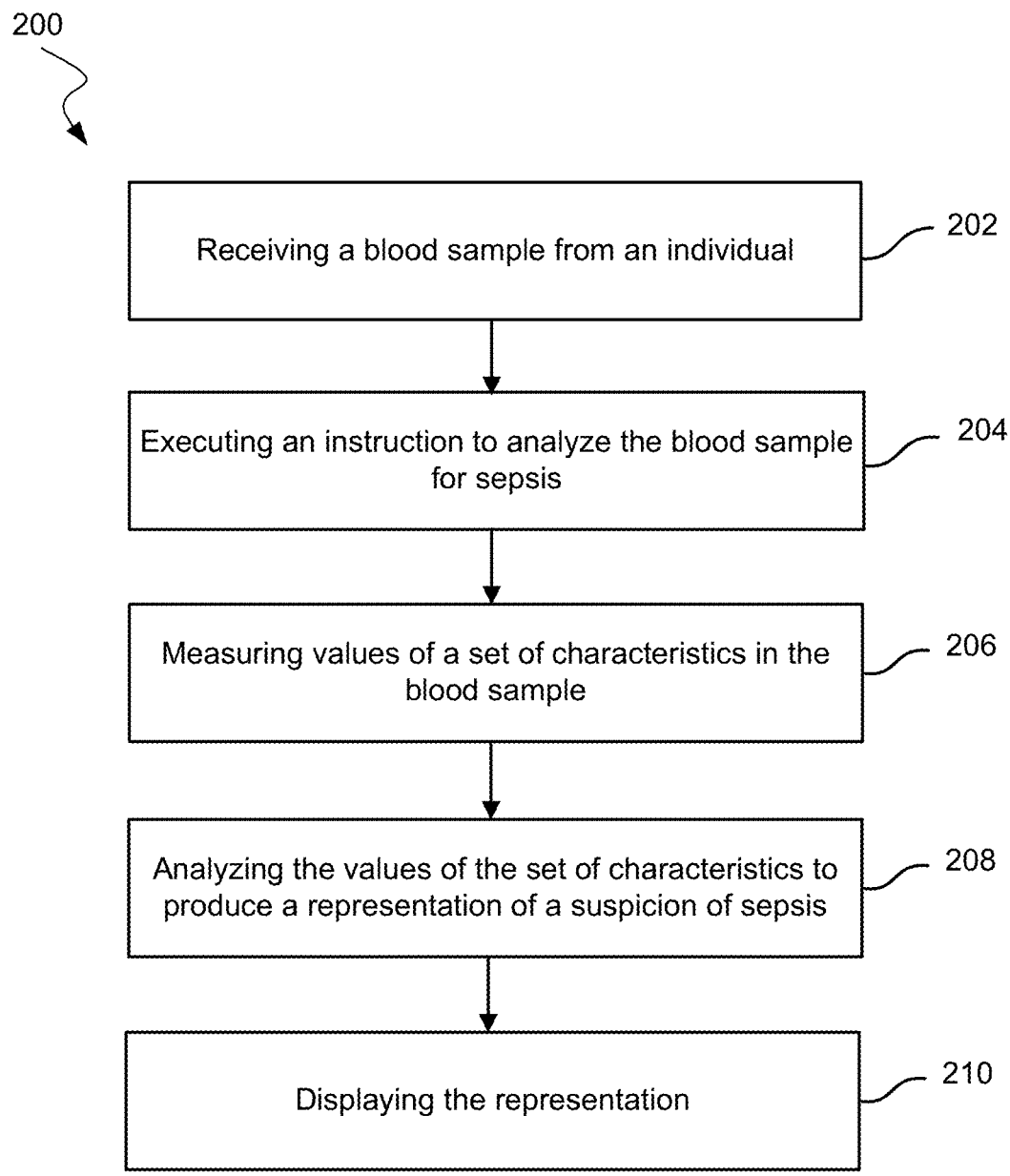
FIG. 2 shows a method for testing a blood sample for sepsis according to embodiments of the present invention.

FIG. 2 shows a method 200 for testing a blood sample for sepsis. Suspicion of sepsis could first arise from or a hypothesis of sepsis could be challenged by testing different kinds of patient samples, such as urine, cerebrospinal fluid, peritoneal fluid, semen, sputum, sweat, amniotic fluid, synovial fluid, pleural fluid, feces, dialysate, serous fluid, or combinations thereof. Additionally, or alternatively, if a blood sample is tested, the blood may be whole blood, diluted blood, lysed blood (i.e., blood which has been treated to lyse one or more kinds of cells, potentially making it easier to analyze the remaining cells or the contents of the lysed cells), isolated blood cells, blood plasma, or combinations thereof. Different types of samples may be subjected to similar tests, e.g., tests for the presence or level of a particular protein or biomarker, or may be subjected to different tests. For example, a blood sample from a patient may be tested for cell population parameters indicative of sepsis, and a sputum sample from the same patient may be cultured and/or tested to look for pathogens that could be the source of an infection.

At block 202, method 200 may include receiving a blood sample from an individual. Method 200 may also include obtaining the blood sample from the individual. The individual may be a patient in an medical facility, including a hospital emergency department.

At block 204, method 200 may also include executing an instruction to analyze the blood sample for sepsis. The method may be executed by a computer system.

Method 200 may further include receiving the instruction to analyze the blood sample for sepsis. The instruction may be received before executing the instruction at block 204. Receiving the instruction may include receiving an input from a medical practitioner to analyze the blood sample for sepsis for the individual. The input may be a computer input indicating that the sample should be analyzed for sepsis for the particular individual. In other embodiments, the input may be a setting that multiple blood samples from multiple individuals, should be analyzed for sepsis. The setting may be the default setting for an analysis system.

In some embodiments, method 200 may include generating the instruction to analyze the blood sample for sepsis. Method 200 may include measuring values of a base set of characteristics in a blood sample. The blood sample may be the same or different as the blood sample analyzed for sepsis. The values of the base set of characteristics may be compared with a set of cutoff values. The comparison may be to determine if the value exceeds a cutoff value. The value may be determined to be higher than the cutoff value or lower than the cutoff value. The cutoff values may be determined from control samples from individuals known to not have sepsis or known to have sepsis. The cutoff value may be 1, 2, or 3 standard deviations from the mean average measured for the control sample. Based on the comparison, the instruction to analyze the blood sample may be generated. The instruction may include a command to analyze the values of another set of characteristics to produce a representation of suspicion of sepsis.

In some embodiments, the instruction to analyze the blood sample for sepsis may be generated after analyzing another blood sample from the individual. In this manner, at least two blood samples from the individual may be analyzed. The same or different set of characteristics may be measured and analyzed from the blood samples.

At block 206, method 200 may include measuring values of a set of characteristics in the blood sample. The set of characteristics being determined prior to measuring the values and may be different from the base set of characteristics. The set of characteristics may be characteristics that are observed to be related to likelihood or suspicion of sepsis. The set of characteristics may include standard deviation of monocyte volume (monocyte distribution width), white blood cell count, neutrophil percentage or amonocyte percentage. The set of characteristics may include any parameter from a complete blood cell count (CBC) module or volume conductivity scatter (VCS) data or any parameter described herein. Measuring the set of characteristics may include performing the tests in FIG. 1.

Measuring the values of the set of characteristics may be for a plurality of types of cells in the blood sample and for a number of cells for each type. The types of cells and the number of cells of each type may be determined using the instruction to analyze the blood sample for sepsis. The types of cells and the number of cells of each type may be a custom behavior for a sepsis panel. In some instruments, the number of cells measured may be controlled, e.g., to ensure that a sufficient number of a certain type of cells is tested to get a statistically reliable result. The number of cells to be measured may be confirmed by counting individual cells, or, in some instruments, may be inferred by controlling the volume and dilution (or non-dilution) of the analyzed sample, which will generally be proportionate to the number of cells in the sample. That is, testing a higher volume of blood will generally result in testing more cells.

At block 208, method 200 may further include analyzing the values of the set of characteristics to produce a representation of a suspicion of sepsis. The representation may include a visualization of the values of the set of characteristics for the blood sample and of values for the set of characteristics for a non-septic condition. For example, the visualization may be a graph of values of the set of characteristics for sepsis compared to values of the set of characteristics for non-septic conditions, which may be based, for example, on control samples or a database of values for patients who were determined not to be septic.

Analyzing the values of the set of characteristics to produce the representation may include using a formula to calculate a model value. The formula may include $$\frac{1}{1+e^{-x}},$$

where x is calculated using the values of the set of characteristics. The variable x may be the value of a characteristic (e.g., white blood cell count) or a calculation of multiple values of characteristics (e.g., a linear combination of WBC and SD-V-MO). This formula is exemplary, and one of skill in the art will appreciate that a variety of formulas may be useful, including linear or non-linear mathematical functions. The specific formula used will depend on the characteristics evaluated, both individually and as a group, and may also vary based on institutional preferences (e.g., a hospital's preference to err on the side of incorrectly diagnosing a patient with sepsis versus incorrectly diagnosing a patient as not having sepsis), and, if used, local modifications based on the patient population, user preferences, prevalence of sepsis and related conditions, and the like.

The representation of the suspicion of sepsis may include a comparison of a likelihood of sepsis to a likelihood of a non-septic condition. The representation may be a word cloud with the font size, color, saturation, transparency, shading, emphasis, and/or other visual presentation of each condition correlated with the likelihood of the condition.

The representation of the suspicion of sepsis may include a value of an index corresponding to a likelihood of sepsis. The value of the index may range from a lower value to a higher value. One end of the range of the value of the index may be zero or low likelihood of sepsis. The other end of the range of the value of the index may be a high likelihood of sepsis. Example ranges include from 0 to 1 and from 0 to 100. The range may scale linearly, logarithmically, or non-linearly with the likelihood of sepsis.

In some embodiments, the representation may be displayed against a second representation produced by analyzing second values of the set of characteristics. The second values may be measured from a second, prior blood sample from the individual before analyzing the first, current blood sample. In this manner, the likelihood of sepsis as time progresses may be understood. The time between measuring the first blood sample and the second blood sample may be from 10 minutes to 1 hour, from 1 hour to 2 hours, from 2 hours to 5 hours, from 5 hours to 12 hours, from 12 hours to 24 hours, from 24 hours to 48 hours, or greater than 48 hours.

Method 200 may include running a panel for a non-septic condition (e.g., malaria, leukemia, anemia, lymphoma, leukocytosis, thrombocytopenia). Method 200 may include measuring values of a second set of characteristics in the blood sample. The second set of characteristics may be determined prior to measuring the values of the second set of characteristics. The values of the second set of characteristics may be analyzed to produce a second representation of a non-septic condition. The second representation may be displayed. The second representation may be a suspicion of the non-septic condition. For example, the second representation may be an element in a word cloud, showing the likelihood of the non-septic condition using font size or other visual representations. The second representation may be any representation for suspicion of sepsis described herein but applied for the non-septic condition.

At block 210, method 200 may include displaying the representation. Displaying the representation may be on a computer monitor, phone screen, smart watch screen, a mobile device screen, or a hard copy. In some embodiments, method 200 may include determining, based on the representation, whether sepsis is suspected or likely. Upon determining that sepsis is suspected or likely, a second number of cells in the blood sample may be analyzed. The second number of cells may be greater than the first number of cells measured to generate the initial representation. The cells in the second number of cells may include cells in the first number of cells. Second values of the set of characteristics in the blood sample may be measured, with the second values associated with the second number of cells. The second values may be analyzed to produce a second representation of the suspicion of sepsis. The second representation may be displayed. Alternately or additionally, the second set of cells may be analyzed for a second characteristic or second set of characteristics, for example, for characterization of a different population of cells (e.g., red blood cells vs. white blood cells, neutrophils vs. monocytes, immature vs. mature cells, etc.), or a different population measurement (e.g., a minimum size, volume, granularity, etc., a standard deviation for a particular measurement, a range for the measurements of a particular type, etc.) or may be a characterization of a different feature of the patient sample than the patient's cells, such as chemistry, immunoassay, microbiology, etc. (e.g., PCT, CRP, ESR, serum lactate, microbial culture, flu test or other viral indication or identification, fungal culture, or combinations thereof).

Method 200 may include determining, based on the representation, a likelihood of sepsis. Upon determining that sepsis is likely, method 200 may include treating the individual for sepsis. Individuals diagnosed with sepsis may receive closer monitoring, hospital admission, aggressive IV fluids, repeated blood cultures, antibiotic treatment, vitamin (e.g. vitamin C) treatment, and/or prioritized diagnoses and treatment.

Method 200 may also include displaying values of the set of characteristics or other data related to the values of the set of characteristics. For example, the results of laboratory tests or leukocyte cell population data (CPD) may be displayed.

B. Example Characteristics

The set of characteristics can be determined from other analysis for parameters that perform for indicating a suspicion, likelihood, or presence of sepsis. The set of characteristics may include white blood cell count and standard deviation of monocyte volume, as described in U.S. application Ser. No. 16/073,757, titled "INFECTION DETECTION AND DIFFERENTIATION SYSTEMS AND METHODS," filed Jan. 24, 2017 and U.S. Provisional Application No. 62/660,795, titled "SEPSIS INFECTION DETECTION SYSTEMS AND METHODS," filed Apr. 20, 2018.

The characteristics may include parameters that have been analyzed against samples from individuals known to be positive for sepsis against those that are negative for sepsis, including those from individuals without sepsis, including individuals that are healthy, that have an infection, and that have SIRS.

The exemplary parameters described herein as suitable for evaluating sepsis were identified after studying over 250 hematology parameters from different analytical methods such as complete blood count (CBC), nucleated red blood cells (NRBC), leukocyte differential (DIFF), and reticulated cells (RETIC). Various analytical methodologies for counting and/or otherwise characterizing these blood cells are known in the art, including, without limitation, light scatter, fluorescence, image analysis, electrical impedance, flow cytometry, colorimetry, immunoassay, and combinations thereof. These methodologies may, in various embodiments, be performed in whole or in part on whole blood (e.g., a blood sample that has not be diluted, concentrated or otherwise isolated or purified), diluted blood, treated blood (e.g., a blood sample that has been exposed to lysing agents to lyse one or more kinds of cells, or a blood sample that has been treated with a stain or other substance to differentiate different kinds of cells), separate blood fractions (e.g., plasma, serum, various cell fractions), concentrated blood, and the like. As described above, the parameters may be used in combination, for example, based on some combination of SD-EV-MO (standard deviation of monocyte volume in extended data range (volume) mode), WBC' (non-linear transformation of WBC count to include low WBC count as a positive factor), and MO_NE % (summation of monocyte percentage and neutrophil percentage). A high or low value of WBC' can indicate suspicion of sepsis. A possible equation for WBC' is the following:

$$WBC' = 0.5 + 0.5\left[\max\left(\frac{1}{1+e^{-2.5(WBC-11)}}, \frac{1}{1+e^{-2.5(5-WBC)}}\right)\right].$$

Other equations for WBC' that generate a high value of WBC' for low values of WBC and also for high values of WBC may be used.

Based on data sets from a particular hospital over a limited time period, various models were developed to describe a probability of sepsis using parameters that can be measured by a commercial cellular analyzer, such as the Beckman Coulter® DxH® 900 Hematology Analyzer. Any of these parameters or combination of parameters may be a characteristic in the set of characteristics. Linear and logistic models were developed for possible combinations of the parameters. The model used the expression $$\frac{1}{1+e^{-x}},$$

where x may be the value of the parameter itself or a separate model combining two or more parameters. For example, using the DxH® 900 Hematology Analyzer, the model-values for x in Table 1 were found to have clinically useful sensitivity and specificity.

TABLE 1

| Parameters | Suggested Cutoff Value | Model value "x" |
|---|---|---|
| (@SD-V-MO) + (WBC) | ≥0.0651 | (0.336 × @SD-V-MO) + (0.185WBC) − 11.63 |
| (@SD-V-MO) + (MO_NE %) | ≥0.0685 | (0.294 × @SD-V-MO) + (0.139 × MO_NE %) − 20.08 |
| (@SD-V-MO) + (WBC') | ≥0.0679 | (0.339 × @SD-V-MO) + (5.223WBC') − 13.492 |
| (WBC) + (MO_NE %) | ≥0.0771 | (0.097 × WBC) + (0.125 × MO_NE %) − 14.021 |
| (WBC) + (SD-EV-MO) | ≥0.0630 | (0.177 × WBC) + (0.4744 × SD-EV-MO) − 9.777 |
| (MO_NE %) + (WBC') | ≥0.0763 | (0.123 × MO_NE %) + (3.333 × WBC') − 15.1557 |
| (MO_NE %) + SD-EV-MO | ≥0.0653 | (0.1386 × MO_NE %) + (0.421 × SD-EV-MO) − 18.51 |
| (WBC') + (SD-EV-MO) | ≥0.0634 | (4.991 × WBC') + (0.469 × SD-EV-MO) − 11.4 |

The exemplary, suggested cutoff values differentiating sepsis from non-sepsis are based on rough optimization of sensitivity and specificity, trying to strike a balance between correctly ruling out patients who do not have sepsis and correctly identifying patients who do have sepsis. Typically, increasing confidence in one kind of certainty (rule-in or rule-out) decreases certainty in the other. As such, the cutoff actually used may differ for different users, who may have different preferences for whether one kind of error is better or worse than the other. Further, as described above, the cutoff values may be adjusted for different patient populations. These suggested cutoff values could be examples of the cutoff described with method 200 in FIG. 2, or could be a different cutoff. With method 200, the cutoff value may be used to determine whether a blood sample should be analyzed for sepsis. The cutoff value in method 200 may be set conservatively so that more blood samples should be analyzed further for sepsis even if a specific parameter or set of parameters do not show a presence of sepsis with a first analysis.

Other hematology parameters that may be helpful with evaluating sepsis include hemoglobin (Hgb), hematocrit (HCT), red blood cell (RBC), white blood cell (WBC), neutrophil number (NE#), toxic granulation, and platelet (PLT). Exemplary parameters are described in Goyette et al., "Hematologic changes in sepsis and their therapeutic implications," *Seminars in Respiratory and Critical Care Medicine*, Vol. 25, No. 6, pp. 645-659 (2004); Aird, "The hematologic system as a marker of organ dysfunction in sepsis," *Mayo Clin Proc.*, 78:869-81 (2003); and Warner, "Tips for evaluating a peripheral blood smear for possible sepsis," (2014) available at laboratory-manager.advanceweb.com/signs-of-sepsis/. The entire contents of these references are incorporated herein by reference for all purposes. Machine learning may further refine these features, both by identifying interactions between parameters and by identifying parameters and/or interactions that may be more or less relevant in a particular patient population. Further, machine learning may refine which parameters for which cell populations are most relevant, for example, absolute cell counts, relative cell counts, distribution measures (e.g., standard deviation, extrema, mode, median, mean, skewness, normality, modality, symmetry, etc.), or combinations thereof.

Figure 3:
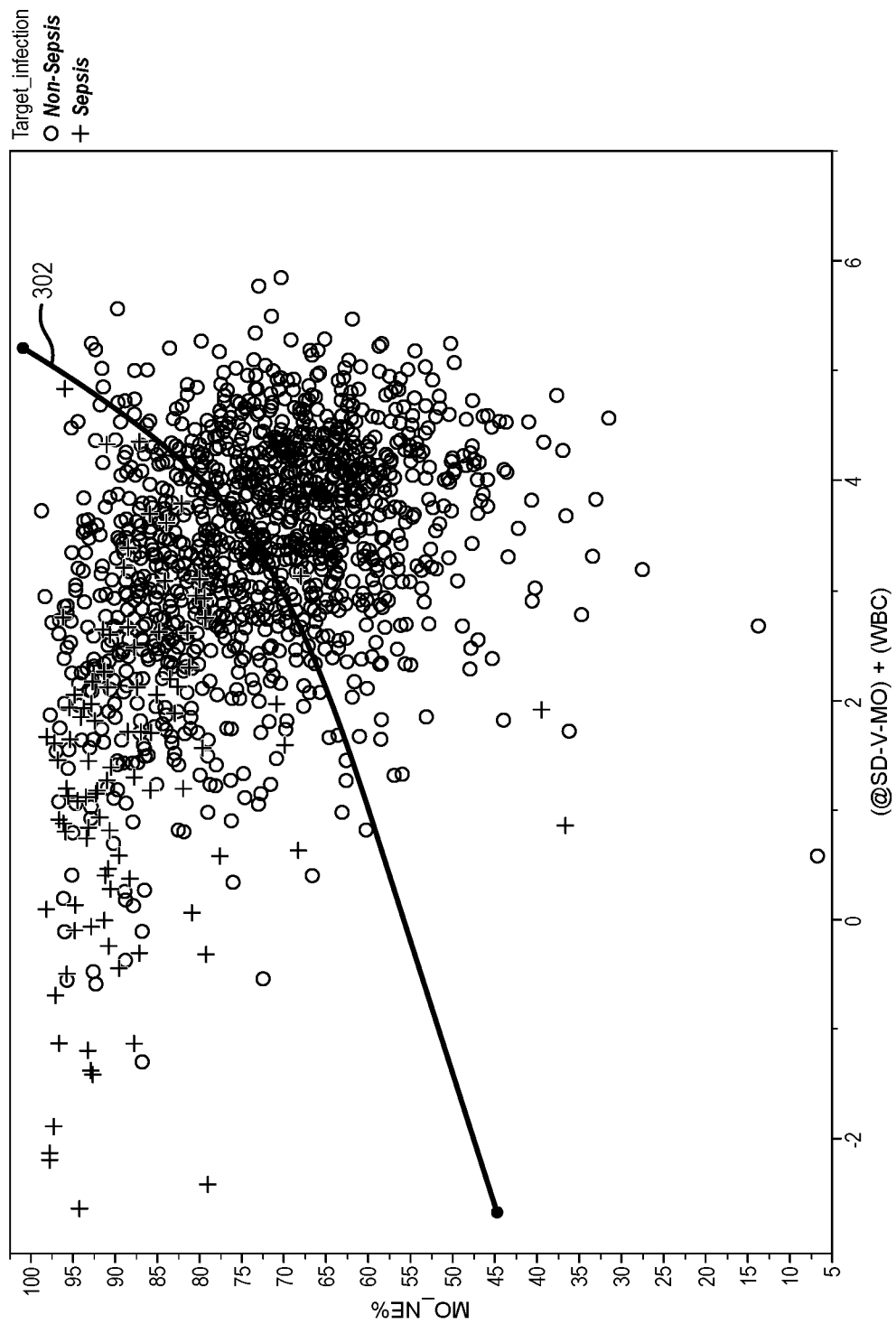
FIG. 3 shows an example of a bi-dimensional mathematical model according to embodiments of the present invention.

A bi-dimensional index mathematical model may be used. FIG. 3 shows an example using an index calculated from MO_NE % and an index calculated from @SD-V-MO and WBC. The index for MO_NE % is shown on the y-axis, and the index for @SD-V-MO and WBC is shown on the x-axis. Data points from individual known to have sepsis are shown with a cross. Data points with those known not to have sepsis are shown with a circle. Line 302 may be used to help identify sepsis in individuals. Most of the data points from individuals with sepsis are above line 302. Data points from individuals known not to have sepsis are also above line 302. Line 302 may therefore not be effective in distinguishing sepsis from non-sepsis. However, line 302 may capture most patients with sepsis. That is, line 302 indicates a suspicion of sepsis. In FIG. 3, only three data points showing sepsis lie underneath line 302. As a result, a blood sample from an individual that results in a data point above line 302 may be considered to have suspicion of sepsis, even if sepsis may be unlikely. If several indices or several models indicate a suspicion of sepsis, additional tests may be run, sepsis may be considered likely, and/or treatment may be started. Line 502 may be defined with respect to one or more parameter-based index. In general, line 502 should be defined to best separate the two classes (sepsis and non-sepsis). This can be done by regression analysis, but may preferentially be done by machine learning, and may be updated periodically based on local (e.g., specific to one laboratory or to the laboratories in one organization, such as a local health system) or aggregated data (e.g., data collected from a plurality of unaffiliated laboratories).

C. Example Panel Results

Figure 4:
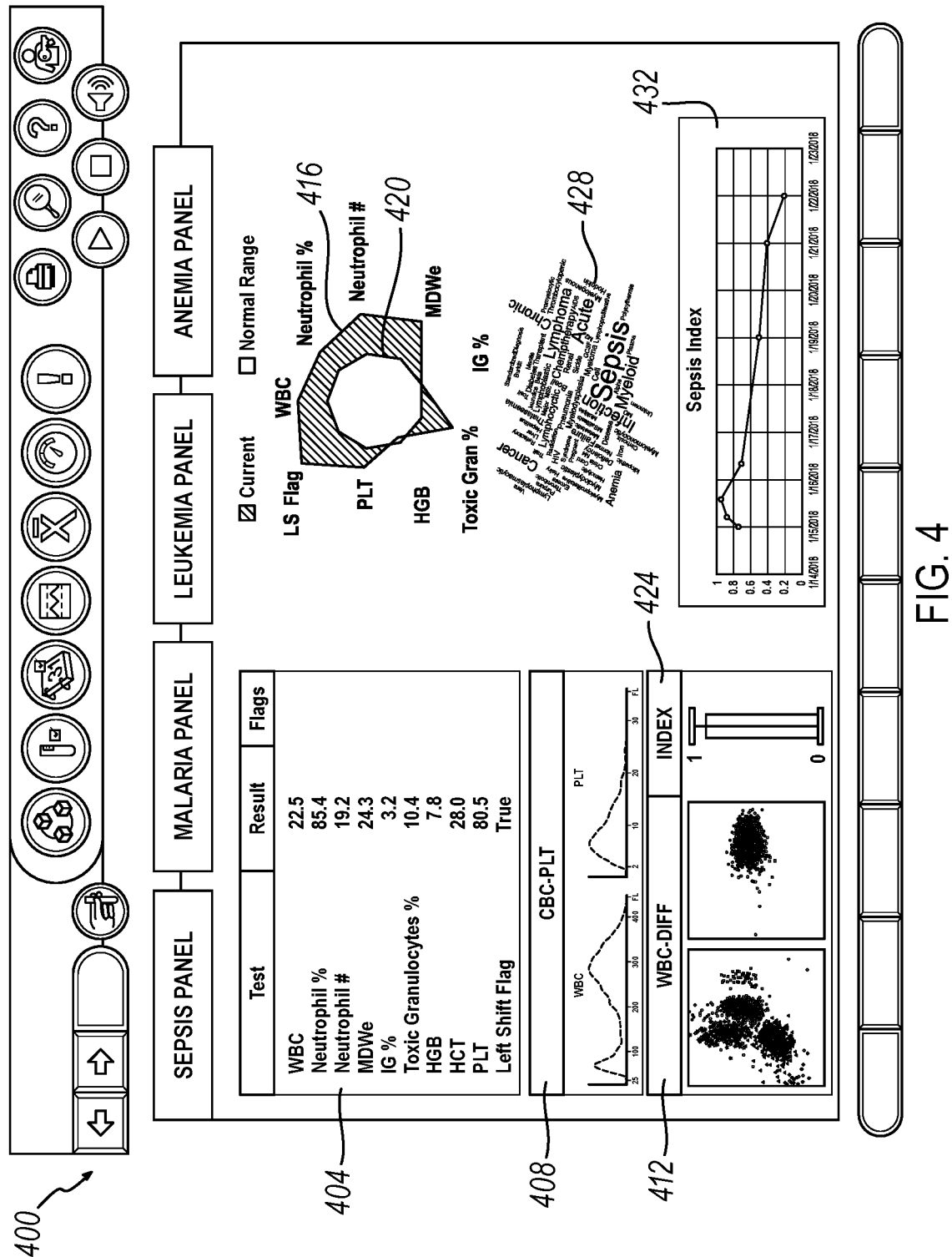
FIG. 4 shows an example user interface according to embodiments of the present invention.

FIG. 4 shows an example user interface 400 displaying results of a sepsis panel. The left side of the user interface 400 includes a table 404 of tests and results. Additional data from tests can be shown, including CBC-PLT 408 and WBC-DIFF 412. CBC-PLT 408 shows the white blood cell count and the platelet count as histograms. WBC-DIFF 412 shows the percentage of different white blood cells present. Graphing cell population data provides visual cues about the patient's health. The shape of the histogram may conform to a typical distribution (which might or might not be "normal" in a statistical sense), or may indicate disturbances in the cell population, and in some cases the nature and/or magnitude of the deviation from a typical histogram may provide clues about the cause or the clinical relevance of the disturbance. User interface 400 may include different representations of the suspicion of sepsis. A radar plot 416 shows the values of certain parameters for the current blood sample compared to the normal range (nonagon 420). If multiple parameters have values outside the normal range, sepsis may be more likely than if fewer parameters have values outside the normal range. Radar plot 416 may be a clear visual depiction of many parameters, allowing a medical practitioner to readily identify an abnormal blood sample, which may have sepsis or may need to be tested further for sepsis, or may justify heightened clinical monitoring (for example, keeping a patient overnight in the hospital instead of sending the patient home) and/or the initiation of medical treatment.

User interface 400 may include an index 424. Index 424 may represent a suspicion of sepsis or a likelihood of sepsis. Index 424 may cover a range. In FIG. 4, index 424 ranges from 0 to 1, with 1 being associated with a higher likelihood of sepsis. The index can be any preferred range or scale, for example, 1-10, 1-100, or alternative indicators such as red-yellow-green color-coding with or without a numerical index.

User interface 400 may also include word cloud 428. Word cloud 428 may include the results from several panels. The font size of the word may be proportional to the likelihood of the condition or a level of concern regarding the condition. Each condition may have an index associated with it after analysis, similar to index 424 for sepsis. Word cloud 428 may be one way to represent index results for different conditions.

In addition, user interface 400 may include a plot 432 of an index for sepsis over time. The trend for sepsis over time may help a medical practitioner determine whether the risk of sepsis is increasing or decreasing. Trending the likelihood of sepsis may be helpful in monitoring the effectiveness of treatment, or may be helpful in monitoring patients who present with mild or inconsistent symptoms before they reach organ failure.

User interface 400 may include different representations of the suspicion or likelihood of sepsis. The user interface may prompt the medical practitioner if treatment for sepsis is desired. If the medical practitioner indicates treatment is desired, the user interface may send an order to another medical practitioner to prepare a treatment. User interface 400 may have the look and feel of the host sepsis panel (e.g., the user interface for a particular laboratory instrument), even with individual representations being linked to other panels (which may typically be accessed on other interfaces of the host instrument, or may which may be acquired from other instruments or other data sources), which may be analyzed according to their own models and calculations. In some aspects, an institution, such as a hospital or medical practice group, or an individual user, may be able to turn on or off different indicators on user interface 400. For example, a medical practitioner may be able to disable word clouds, test tables, or time indices if the practitioner's preferences, practice or patient population make one or more of the visualizations less helpful or distracting.

III. Sepsis Learning Models

Data collected for sepsis panels may be analyzed for patterns to better develop a model or indicator of sepsis. In some instances, the values of parameters may vary from hospital to hospital. Populations near the hospital may have similar diets, a common water source, a certain ethnic makeup, and/or other similarities. As a result, the analysis for suspicion of sepsis may be refined or improved using data collected at specific site or geographic area. Additionally, panels for sepsis are not common and analyzing data generated by new panels may help arrive at an improved analysis for suspicion of sepsis. Analysis of data may be through a machine learning algorithm.

Figure 5:
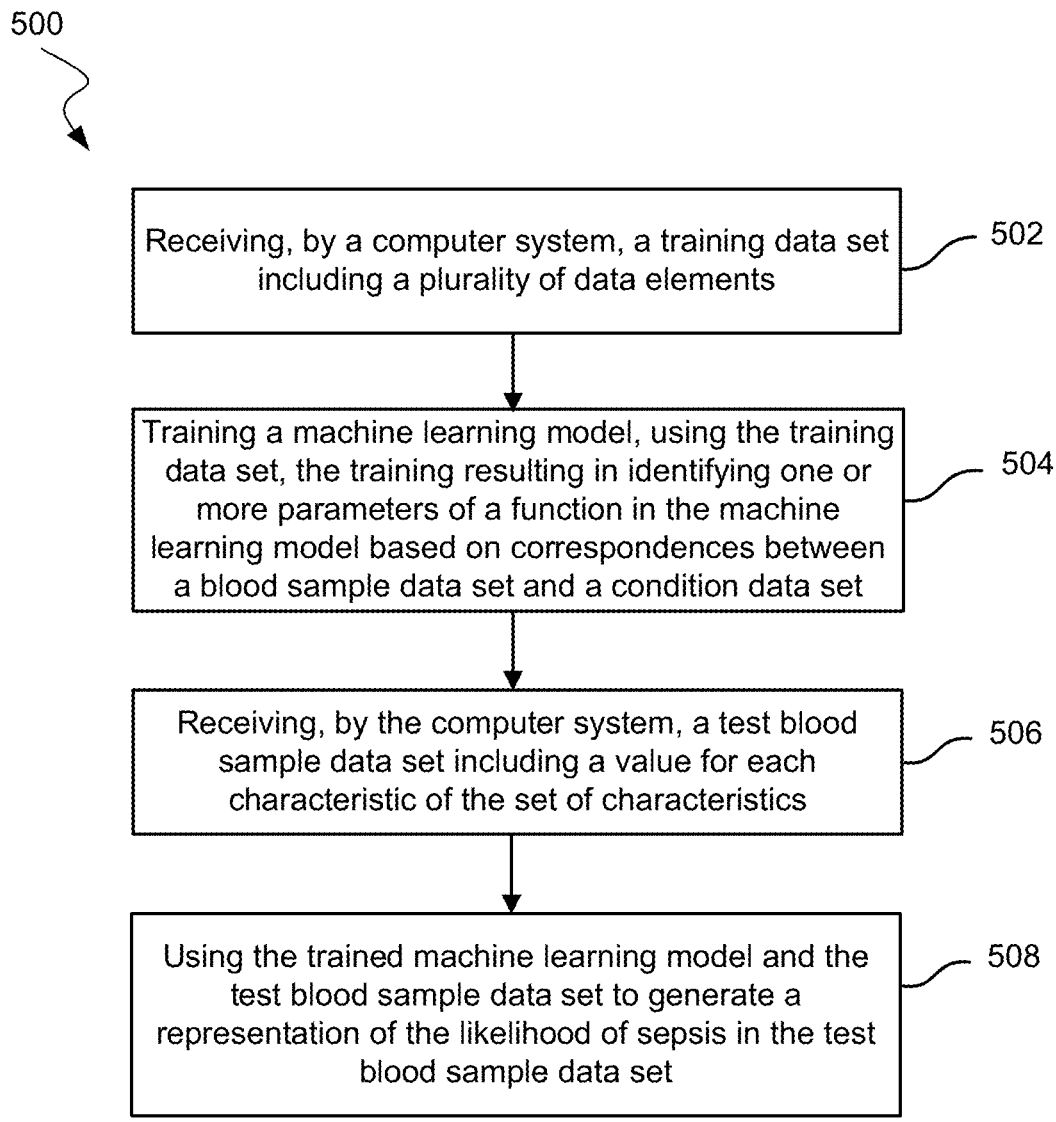
FIG. 5 shows a method of training and using machine learning models to estimate a likelihood of sepsis according to embodiments of the present invention.

FIG. 5 shows a method 500 of training and using machine learning models to estimate a likelihood of sepsis based on test blood sample data sets.

At block 502, method 500 may include receiving, by a computer system, a training data set including a plurality of data elements. Each training data element of the plurality of data elements may include a blood sample data set and a condition data set. The blood sample data set may include, for each individual of a plurality of individuals, values for a set of characteristics associated with a blood sample. The condition data set may indicate a diagnosis of sepsis in each individual of the plurality of individuals, e.g., based on diagnostic codes in the patient's medical records. Because there is no single, definitive biomarker for sepsis, these diagnostic codes reflect a practitioner's best judgment based on clinical signs and symptoms, possibly including laboratory test results.

Method 500 may include measuring values of the set of characteristics in the blood sample for each individual. Method 500 may also include determining a likelihood of sepsis in the individual.

At block 504, method 500 may also include training a machine learning model, using the training data set. The training may result in identifying one or more parameters of a function in the machine learning model based on correspondences between the blood sample data set and the condition data set. The machine learning model may include a convolutional neural network. A set of convolutional filters may depend on the one or more parameters. Training the machine learning model may include identifying one or more parameters for the set of convolutional filters.

At block 506, method 500 may include receiving, by the computer system, a test blood sample data set including a value for each characteristic of the set of characteristics.

At block 508, method 500 may using the trained machine learning model and the test blood sample data set to generate a representation of the likelihood of sepsis in the test blood sample data set.

IV. Systems for Testing for Sepsis

Embodiments of the present technology may include an automated system for testing a blood sample for sepsis. The blood sample may be obtained from an individual. The system may include a first module. The first module may evaluate cells in the blood sample by observing the way light scatters after being passed through the cell. The first module may, additionally or alternatively, include a first assembly configured to measure direct current (DC) impedance of cells of the blood sample passing individually through a cell interrogation zone. The first module may also or alternatively include a second assembly configured to measure radiofrequency (RF) conductivity of cells of the blood sample passing individually through the cell interrogation zone. The first module may include Beckman Coulter's UniCel® DxH™ 800 and/or DxH™ 900 Cellular Analysis System.

Parameters that may be measured in the first module include those listed in Table 1. Any of these parameters may be a characteristic used in methods described herein.

TABLE 1

Cell Population Data parameters

| | Neutrophil NE (ne) | Lymphocyte LY (ly) | Monocyte MO (mo or mn) | Eosinophil EO (eo) | Non-nucleated red blood cell NNRBC (nnr or nnrbc) |
|---|---|---|---|---|---|
| Cell Conductivity (C) high freq. current | SD-C-NE MN-C-NE | SD-C-LY MN-C-LY | SD-C-MO MN-C-MO | SD-C-EO MN-C-EO | SD-C-NNRBC MN-C-NNRBC |
| Cell Volume (V) low freq. current | SD-V-NE MN-V-NE | SD-V-LY MN-V-LY | SD-V-MO MN-V-MO | SD-V-EO MN-V-EO | SD-V-NNRBC MN-V-NNRBC |
| Axial light loss or absorbed light (AL2 or ALL) | SD-AL2-NE MN-AL2-NE | SD-AL2-LY MN-AL2-LY | SD-AL2-MO MN-AL2-MO | SD-AL2-EO MN-AL2-EO | SD-AL2-NNRBC MN-AL2-NNRBC |
| Low-angle light scatter (LALS) | SD-LALS-NE MN-LALS-NE | SD-LALS-LY MN-LALS-LY | SD-LALS-MO MN-LALS-MO | SD-LALS-EO MN-LALS-EO | SD-LALS-NNRBC MN-LALS-NNRBC |
| Upper median-angle light scatter (UMALS) | SD-UMALS-NE MN-UMALS-NE | SD-UMALS-LY MN-UMALS-LY | SD-UMALS-MO MN-UMALS-MO | SD-UMALS-EO MN-UMALS-EO | SD-UMALS-NNRBC MN-UMALS-NNRBC |
| Lower median-angle light scatter (LMALS) | SD-LMALS-NE MN-LMALS-NE | SD-LMALS-LY MN-LMALS-LY | SD-LMALS-MO MN-LMALS-MO | SD-LMALS-EO MN-LMALS-EO | SD-LMALS-NNRBC MN-LMALS-NNRBC |
| Median-angle light scatter (MALS) [UMALS + LMALS] | SD-MALS-NE MN-MALS-NE | SD-MALS-LY MN-MALS-LY | SD-MALS-MO MN-MALS-MO | SD-MALS-EO MN-MALS-EO | SD-MALS-NNRBC MN-MALS-NNRBC |

In addition, the automated system may include a second module configured to count cells. The second module may implement Coulter technology. The second module may determine complete blood count (CBC) data, including white blood cell count and red blood cell count.

The automated system may also include a data processing module in connectivity with the first module and second module. The data processing module may include a processor and a tangible, non-transitory computer readable medium, the tangible non-transitory computer readable medium programmed with a computer application. The computer application when executed by a processor may cause the processor to execute an instruction to analyze the blood sample for sepsis. The processor may be caused to measure values of a set of characteristics in the blood sample. The set of characteristics may be determined prior to measuring the values. The processor may also be caused to analyze the values of the set of characteristics to produce a representation of a suspicion of sepsis. The processor may further be caused to display the representation. The instruction may include any of the methods described herein.

Figure 6:
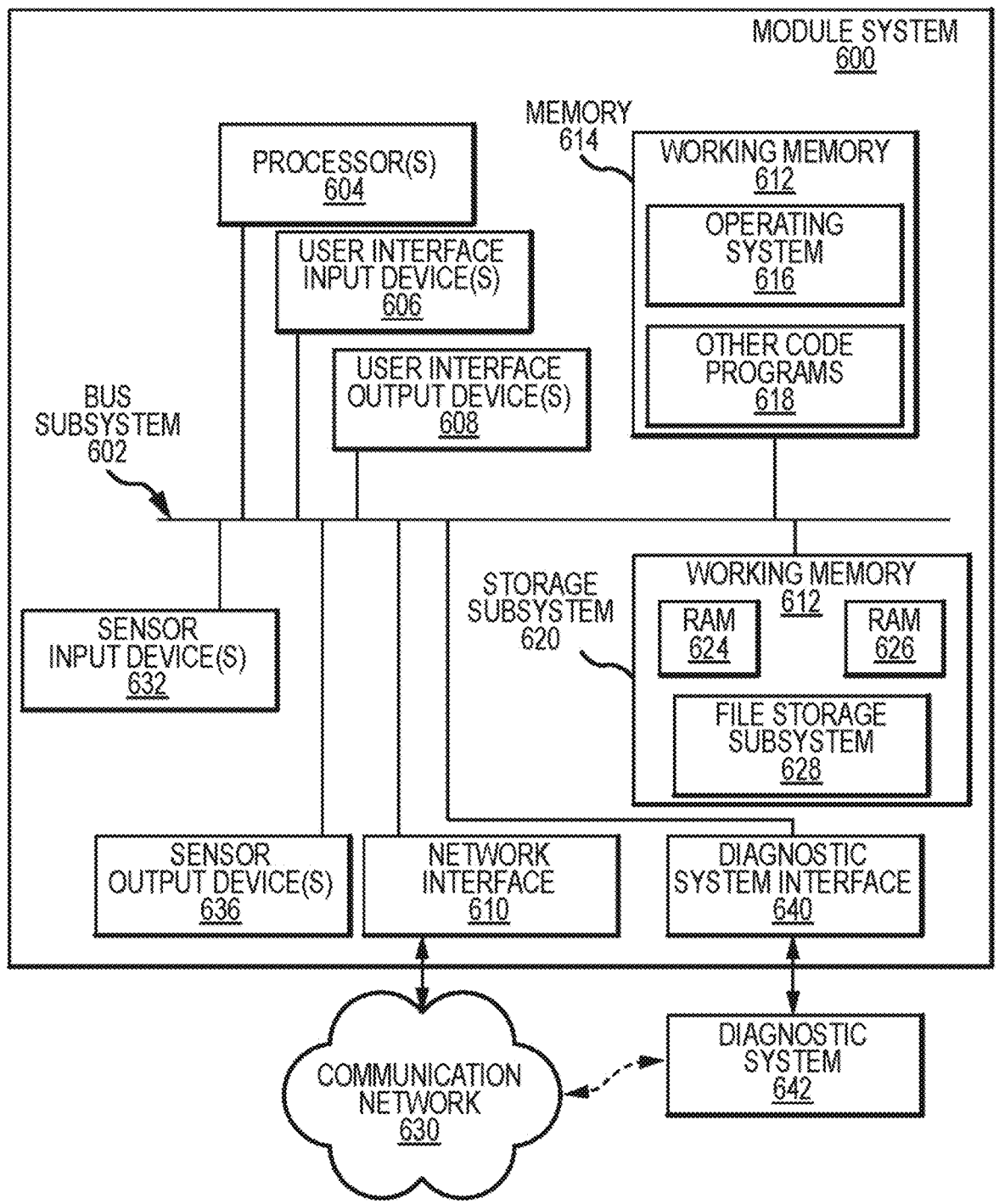
FIG. 6 shows a simplified block diagram of a module system according to embodiments of the present invention.

FIG. 6 is a simplified block diagram of an exemplary module system that broadly illustrates how individual system elements for a module system 600 may be implemented in a separated or more integrated manner. Module system 600 may be part of or in connectivity with a cellular analysis system for evaluating the sepsis status according to embodiments of the present invention. Module system 600 is well suited for producing data or receiving input related to evaluate the infection status. In some instances, module system 600 includes hardware elements that are electrically coupled via a bus subsystem 602, including one or more processors 604, one or more input devices 606 such as user interface input devices, and/or one or more output devices 608 such as user interface output devices. In some instances, system 600 includes a network interface 610, and/or a diagnostic system interface 640 that can receive signals from and/or transmit signals to a diagnostic system 642. In some instances, system 600 includes software elements, for example shown here as being currently located within a working memory 612 of a memory 614, an operating system 616, and/or other code 618, such as a program configured to implement one or more aspects of the techniques disclosed herein. Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing any one or more of the method or process steps described herein.

In some embodiments, module system 600 may include a storage subsystem 620 that can store the basic programming and data constructs that provide the functionality of the various techniques disclosed herein. For example, software modules implementing the functionality of method aspects, as described herein, may be stored in storage subsystem 620. These software modules may be executed by the one or more processors 604. In a distributed environment, the software modules may be stored on a plurality of computer systems and executed by processors of the plurality of computer systems. Storage subsystem 620 can include memory subsystem 622 and file storage subsystem 628. Memory subsystem 622 may include a number of memories including a main random access memory (RAM) 626 for storage of instructions and data during program execution and a read only memory (ROM) 624 in which fixed instructions are stored. File storage subsystem 628 can provide persistent (non-volatile) storage for program and data files, and may include tangible storage media which may optionally embody patient, treatment, assessment, or other data. File storage subsystem 628 may include a hard disk drive, a floppy disk drive along with associated removable media, a Compact Digital Read Only Memory (CD-ROM) drive, an optical drive, DVD, CD-R, CD RW, solid-state removable memory, other removable media cartridges or disks, and the like. One or more of the drives may be located at remote locations on other connected computers at other sites coupled to module system 600. In some instances, systems may include a computer-readable storage medium or other tangible storage medium that stores one or more sequences of instructions which, when executed by one or more processors, can cause the one or more processors to perform any aspect of the techniques or methods disclosed herein. One or more modules implementing the functionality of the techniques disclosed herein may be stored by file storage subsystem 628. In some embodiments, the software or code will provide protocol to allow the module system 600 to communicate with communication network 630. Optionally, such communications may include dial-up or internet, wired or wireless connection communications.

It is appreciated that system 600 can be configured to carry out various aspects of methods of the present invention. In this manner, system 600 is a specialized system. For example, processor component or module 604 can be a microprocessor control module configured to receive cellular parameter signals from a sensor input device or module 632, from a user interface input device or module 606, and/or from a diagnostic system 642, optionally via a diagnostic system interface 640 and/or a network interface 610 and a communication network 630. In some instances, sensor input device(s) may include or be part of a cellular analysis system that is equipped to obtain light angle detection parameters, such as Beckman Coulter's UniCel® DxH™ 800 and/or DxH™ 900 Cellular Analysis System. In some instances, user interface input device(s) 606 and/or network interface 610 may be configured to receive cellular parameter signals generated by a cellular analysis system that is equipped to obtain light angle detection parameters, such as Beckman Coulter's UniCel® DxH™ 800 and/or DxH™ 900 Cellular Analysis System. In some instances, diagnostic system 642 may include or be part of a cellular analysis system that is equipped to obtain light angle detection parameters, such as Beckman Coulter's UniCel® DxH™ 800 and/or DxH™ 900 Cellular Analysis System. In some instances, one or more of these systems may obtain multiple light angle detection parameters.

In some instances, system 600 may include multiple analytical sub-systems, including, without limitation, a cellular analysis instrument, a microbiological instrument, a chemical analysis instrument, an immunoassay instrument, or combinations thereof, including possible multiple instruments of the same or different types. In some instances, the analytical sub-systems may be physically networked, such that patient samples could be automatically reflexed by system 600 to different instruments of the same or different types.

Processor component or module 604 can also be configured to transmit cellular parameter signals, optionally processed according to any of the techniques disclosed herein, to sensor output device or module 636, to user interface output device or module 608, to network interface device or module 610, to diagnostic system interface 640, or any combination thereof. Each of the devices or modules according to embodiments of the present invention can include one or more software modules on a computer readable medium that is processed by a processor, or hardware modules, or any combination thereof. Any of a variety of commonly used platforms, such as Windows, Mac, and Unix, along with any of a variety of programming languages, may be used to implement embodiments of the present invention.

User interface input devices 606 may include, for example, a touchpad, a keyboard, pointing devices such as a mouse, a trackball, a graphics tablet, a scanner, a joystick, a touchscreen incorporated into a display, audio input devices such as voice recognition systems, microphones, and other types of input devices. User input devices 606 may also download a computer executable code from a tangible storage media or from communication network 630, the code embodying any of the methods or aspects thereof disclosed herein. It will be appreciated that terminal software may be updated from time to time and downloaded to the terminal as appropriate. In general, use of the term "input device" is intended to include a variety of conventional and proprietary devices and ways to input information into module system 600.

User interface output devices 606 may include, for example, a display subsystem, a printer, a fax machine, or non-visual displays such as audio output devices. The display subsystem may be a cathode ray tube (CRT), a flat-panel device such as a liquid crystal display (LCD), a light-emitting diode (LED) display, an organic light-emitting diode (OLED) display, a plasma display, a projection device, or the like. The display subsystem may also provide a non-visual display such as via audio output devices. In general, use of the term "output device" is intended to include a variety of conventional and proprietary devices and ways to output information from module system 600 to a user. The results of any method or operation described herein (e.g. an infection status) may be displayed on an output device.

Bus subsystem 602 provides a mechanism for letting the various components and subsystems of module system 600 communicate with each other as intended or desired. The various subsystems and components of module system 600 need not be at the same physical location but may be distributed at various locations within a distributed network. Although bus subsystem 602 is shown schematically as a single bus, alternate embodiments of the bus subsystem may utilize multiple busses.

Network interface 610 can provide an interface to an outside network 630 or other devices. Outside communication network 630 can be configured to effect communications as needed or desired with other parties. It can thus receive an electronic packet from module system 600 and transmit any information as needed or desired back to module system 600. As depicted here, communication network 630 and/or diagnostic system interface 642 may transmit information to or receive information from a diagnostic system 642 that is equipped to obtain one or more light angle detection parameters, such as Beckman Coulter's UniCel® DxH™ 800 or DxH™ 900 Cellular Analysis System.

In addition to providing such infrastructure communications links internal to the system, the communications network system 630 may also provide a connection to other networks such as the internet and may comprise a wired, wireless, modem, and/or other type of interfacing connection.

It will be apparent to the skilled artisan that substantial variations may be used in accordance with specific requirements. For example, customized hardware might also be used and/or particular elements might be implemented in hardware, software (including portable software, such as applets), or both. Further, connection to other computing devices such as network input/output devices may be employed. Module terminal system 600 itself can be of varying types including a computer terminal, a personal computer, a portable computer, a workstation, a network computer, or any other data processing system. Due to the ever-changing nature of computers and networks, the description of module system 600 depicted in FIG. 6 is intended only as a specific example for purposes of illustrating one or more embodiments of the present invention. Many other configurations of module system 600 are possible having more or less components than the module system depicted in FIG. 6. Any of the modules or components of module system 600, or any combinations of such modules or components, can be coupled with, or integrated into, or otherwise configured to be in connectivity with, any of the cellular analysis system embodiments disclosed herein. Relatedly, any of the hardware and software components discussed above can be integrated with or configured to interface with other medical assessment or treatment systems used at other locations.

In some embodiments, the module system 600 can be configured to receive one or more cellular analysis parameters of a patient at an input module. Cellular analysis parameter data can be transmitted to an assessment module where an infection status is evaluated, predicted, analyzed, or determined. The infection status can be output to a system user via an output module. In some cases, the module system 600 can determine an initial treatment or induction protocol for the patient, based on one or more cellular analysis parameters and/or the evaluated infection status, for example by using a treatment module. The treatment can be output to a system user via an output module. Optionally, certain aspects of the treatment can be determined by an output device, and transmitted to a treatment system or a sub-device of a treatment system. Any of a variety of data related to the patient can be input into the module system, including age, weight, sex, treatment history, medical history, and the like. Parameters of treatment regimens or diagnostic evaluations can be determined based on such data.

Relatedly, in some instances a system includes a processor configured to receive the cell population data as input. Optionally, a processor, storage medium, or both, may be incorporated within a hematology or cellular analysis machine. In some instances, the hematology machine may generate cell population data or other information for input into the processor. In some instances, a processor, a storage medium, or both, can be incorporated within a computer, and the computer can be in communication with a hematology machine. In some instances, a processor, a storage medium, or both, can be incorporated within a computer, and the computer can be in remote communication with a hematology machine via a network.

Further variations on, and features for, the inventors' technology will be immediately apparent to, and could be practiced without undue experimentation by, those of ordinary skill in the art in light of this disclosure. Accordingly, instead of limiting the protection accorded by this document, or by any document which is related to this document, to the material explicitly disclosed herein, the protection should be understood to be defined by the claims, if any, set forth herein or in the relevant related document when the terms in those claims which are listed below under the label "Explicit Definitions" are given the explicit definitions set forth therein, and the remaining terms are given their broadest reasonable interpretation as shown by a general purpose dictionary. To the extent that the interpretation which would be given to such claims based on the above disclosure is in any way narrower than the interpretation which would be given based on the "Explicit Definitions" and the broadest reasonable interpretation as provided by a general purpose dictionary, the interpretation provided by the "Explicit Definitions" and broadest reasonable interpretation as provided by a general purpose dictionary shall control, and the inconsistent usage of terms in the specification or priority documents shall have no effect.

Explicit Definitions

When appearing in the claims, a statement that something is "based on" something else should be understood to mean that something is determined at least in part by the thing that it is indicated as being "based on." When something is required to be completely determined by a thing, it will be described as being "based exclusively on" the thing.

When used in the claims, "determining" should be understood to refer to generating, selecting, defining, calculating or otherwise specifying something. For example, to obtain an output as the result of analysis would be an example of "determining" that output. As a second example, to choose a response from a list of possible responses would be a method of "determining" a response. As a third example, to identify data received from an external source (e.g., a microphone) as being a thing would be an example of "determining" the thing.

When used in the claims a "means for determining one or more tests and test performance behaviors to detect a specified condition" should be understood as a means plus function limitation as provided for in 35 U.S.C. § 112(f), in which the function is "determining one or more tests and test performance behaviors to detect a specified condition" and the corresponding structure is a computer configured to perform processes as illustrated in FIGS. 1 and 5 and described in the corresponding text.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the particle" includes reference to one or more particles and equivalents thereof known to those skilled in the art, and so forth. The invention has now been described in detail for the purposes of clarity and understanding. However, it will be appreciated that certain changes and modifications may be practiced within the scope of the appended claims.

All publications, patents, and patent applications cited herein are hereby incorporated by reference in their entirety for all purposes. None is admitted to be prior art.

What is claimed is:

1. A method for improving patient outcomes associated with testing a blood sample for sepsis, the method comprising:
    receiving a blood sample from an individual;
    based on an instruction to analyze the blood sample for sepsis, measuring values of a set of characteristics in the blood sample by performing acts comprising:
        passing cells from the blood sample through an interrogation zone of an analyzer;
        illuminating the cells of the blood sample passed through the interrogation zone of the analyzer;
        detecting illumination from the interrogation zone of the analyzer as the cells of the blood sample are passed through the interrogation zone;
        wherein, the set of characteristics is determined prior to measuring the values; and
    displaying a representation of a suspicion of sepsis based on the values of the set of characteristics in a visual interface, wherein the visual interface illustrates a non-septic condition separately from the representation of the suspicion of sepsis;
    wherein:
        the interface comprises a comparison of a likelihood of sepsis to a likelihood of the non-septic condition;
        the non-septic condition is a disorder other than sepsis;
        the comparison of the likelihood of sepsis to the likelihood of the non-septic condition comprises a juxtaposition of the representation of the suspicion of sepsis with a representation of likelihood of the non-septic condition; and
        the representation of the suspicion of sepsis and the representation of likelihood of the non-septic condition are displayed with a visual attribute reflecting the relative likelihood of sepsis and the likelihood of the non-septic condition.

2. The method of claim 1, wherein the set of characteristics comprises at least one of a standard deviation of monocyte volume or white blood cell count.

3. The method of claim 1, further comprising:
    receiving the instruction to analyze the blood sample for sepsis, wherein receiving the instruction comprises receiving an input from a medical practitioner to analyze the blood sample for sepsis for the individual.

4. The method of claim 1, wherein:
    the set of characteristics is a first set of characteristics, and the method further comprises:
    measuring values of a second set of characteristics in the blood sample, the second set of characteristics being different from the first set of characteristics,
    comparing the values of the second set of characteristics with a set of cutoff values, and
    based on the comparison, generating the instruction to analyze the blood sample for sepsis, the instruction including a command to analyze the values of the first set of characteristics to produce the representation of the suspicion of sepsis.

5. The method of claim 1, wherein the interface comprises a visualization of the values of the set of characteristics for the blood sample and of values for the set of characteristics for the non-septic condition.

6. The method of claim 1, wherein:
    the set of characteristics is a first set of characteristics, and the representation is a first representation, and the method further comprising:
    measuring values of a second set of characteristics in the blood sample, the second set of characteristics being determined prior to measuring the values of the second set of characteristics,
    analyzing the values of the second set of characteristics to produce a second representation of a non-septic condition, and
    displaying the second representation.

7. The method of claim 1, wherein the representation of the suspicion of sepsis comprises a value of an index corresponding to a likelihood of sepsis.

8. The method of claim 1, wherein:
    the blood sample is a first blood sample,
    the method further comprising:
        generating the instruction to analyze the first blood sample for sepsis after analyzing a second blood sample from the individual, the second blood sample having been obtained from the individual before the first blood sample.

9. The method of claim 1, wherein:
the representation is a first representation,
the blood sample is a first blood sample, and
the values are first values, and
the method further comprising:
    receiving a second blood sample from the individual;
    measuring second values of the set of characteristics in the second blood sample before measuring the first values of the set of characteristics of the first blood sample;
    producing a second representation based on analyzing the second values of the set of characteristics; and
    displaying the second representation and the first representation.

10. The method of claim 1, further comprising:
obtaining the blood sample from the individual.

11. The method of claim 1, further comprising:
determining, based on the representation, a likelihood of sepsis, and
treating the individual for sepsis.

12. The method of claim 1, wherein:
the values are first values,
measuring the first values in the blood sample comprises analyzing a first number of cells in the blood sample, and
the representation is a first representation,
the method further comprising:
determining, based on the representation, a likelihood of sepsis,
analyzing a second number of cells in the blood sample, the second number of cells being greater than the first number of cells,
upon determining the likelihood of sepsis, measuring second values of the set of characteristics in the blood sample, the second values being associated with the second number of cells,
analyzing the second values of the set of characteristics to produce a second representation of the suspicion of sepsis, and
displaying the second representation.

13. The method of claim 1, wherein analyzing the values of the set of characteristics to produce the representation comprises transforming a value which can be any value from negative infinity to positive infinity to a [0,1] range.

14. The method of claim 1, wherein:
measuring the values of the set of characteristics comprises measuring:
    a plurality of types of cells in the blood sample, and
    a number of cells for each type,
the types of cells are determined based on an instruction to analyze the blood sample for sepsis, and
the number of cells of each type is determined based on the instruction to analyze the blood sample for sepsis.

15. A system for improving patient outcomes associated with testing a blood sample for sepsis, the system comprising an analyzer comprising:
an interrogation zone;
one or more light sources adapted to illuminate cells of the blood sample passed through the interrogation zone;
one or more light detectors adapted to detect light from the interrogation zone as the cells of the blood sample are passed through the interrogation zone;
a processor programmed with instructions to perform acts comprising:
    measuring values of a set of characteristics in the blood sample; and
    displaying a representation of a suspicion of sepsis based on the values of the set of characteristics in a visual interface, wherein the visual interface illustrates a non-septic condition separately from the representation of the suspicion of sepsis;
wherein:
    the interface comprises a comparison of a likelihood of sepsis to a likelihood of the non-septic condition;
    the non-septic condition is a disorder other than sepsis;
    the comparison of the likelihood of sepsis to the likelihood of the non-septic condition comprises a juxtaposition of the representation of the suspicion of sepsis with a representation of likelihood of the non-septic condition; and
    the representation of the suspicion of sepsis and the representation of likelihood of the non-septic condition are displayed with a visual attribute reflecting the relative likelihood of sepsis and the likelihood of the non-septic condition.

\* \* \* \* \*